(12) United States Patent
Stewart et al.

(10) Patent No.: US 9,272,069 B2
(45) Date of Patent: *Mar. 1, 2016

(54) ADHESIVE COMPLEX COACERVATES AND METHODS OF MAKING AND USING THEREOF

(75) Inventors: Russell Stewart, Salt Lake City, UT (US); Hui Shao, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 836 days.

This patent is subject to a terminal disclaimer.

(21) Appl. No.: 12/864,045

(22) PCT Filed: Nov. 13, 2008

(86) PCT No.: PCT/US2008/083311
§ 371 (c)(1),
(2), (4) Date: Jul. 22, 2010

(87) PCT Pub. No.: WO2009/094060
PCT Pub. Date: Jul. 30, 2009

(65) Prior Publication Data
US 2010/0305626 A1    Dec. 2, 2010

Related U.S. Application Data

(60) Provisional application No. 61/023,173, filed on Jan. 24, 2008.

(51) Int. Cl.
| C08F 230/02 | (2006.01) |
| C08F 8/06 | (2006.01) |
| C08F 8/00 | (2006.01) |
| C09J 133/14 | (2006.01) |
| A61L 24/00 | (2006.01) |
| A61L 24/04 | (2006.01) |
| A61L 27/26 | (2006.01) |
| A61L 27/54 | (2006.01) |

(52) U.S. Cl.
CPC ........... *A61L 24/0015* (2013.01); *A61L 24/043* (2013.01); *A61L 27/26* (2013.01); *A61L 27/54* (2013.01); *C09J 133/14* (2013.01); *A61L 2300/412* (2013.01); *A61L 2300/602* (2013.01); *A61L 2300/62* (2013.01); *C08F 2800/10* (2013.01); *C08F 2810/20* (2013.01); *C08F 2810/30* (2013.01)

(58) Field of Classification Search
None
See application file for complete search history.

(56) References Cited

U.S. PATENT DOCUMENTS

| 3,458,460 A | 7/1969 | Shepard et al. |
| 3,947,396 A | 3/1976 | Kangas et al. |
| 3,950,296 A | 4/1976 | Kangas et al. |
| 4,767,463 A * | 8/1988 | Brode et al. ............... 106/162.2 |
| 4,913,743 A * | 4/1990 | Brode et al. ............... 106/162.2 |
| 5,529,914 A | 6/1996 | Hubbell et al. |
| 6,312,725 B1 | 11/2001 | Wallace et al. |
| 6,428,978 B1 | 8/2002 | Olsen et al. |
| 6,497,729 B1 | 12/2002 | Moussy et al. |
| 6,568,398 B2 | 5/2003 | Cohen |
| 6,916,488 B1 | 7/2005 | Meier et al. |
| 7,622,533 B2 | 11/2009 | Lee |
| 8,283,384 B2 | 10/2012 | Stewart et al. |
| 2001/0056301 A1 | 12/2001 | Goupil et al. |
| 2002/0006886 A1 * | 1/2002 | Beerse et al. ................. 510/295 |
| 2002/0164364 A1 | 11/2002 | Quong |
| 2002/0169476 A1 | 11/2002 | Cohen et al. |
| 2003/0023000 A1 | 1/2003 | Bavouzet et al. |
| 2004/0013738 A1 | 1/2004 | Voigt et al. |
| 2004/0086479 A1 | 5/2004 | Grinstaff et al. |

(Continued)

FOREIGN PATENT DOCUMENTS

| CN | 1341032 | 3/2002 |
| CN | 1446590 | 10/2003 |

(Continued)

OTHER PUBLICATIONS

The Tube Cement of Phragmatopoma californica: a solid foam, Stewart et al., Oct. 11, 2004, Journal of Experimental Biology, 207,4727-4734.*

(Continued)

*Primary Examiner* — Peter A Salamon
(74) *Attorney, Agent, or Firm* — Gardner Groff Greenwald & Villanueva, PC

(57) ABSTRACT

Described herein is the synthesis of adhesive complex coacervates. The adhesive complex coacervates are composed of a mixture of one or more polycations, one or more polyanions, and one of more multivalent cations. The polycations and polyanions in the adhesice complex coacervate are crosslinked with one another by covalent bonds upon curing. The adhesive complex coacervates have several desirable features when compared to conventional bioadhesives, which are effective in water-based applicatgions. The adhesive complex coacervates described herein exhibit good interfacial tension in water when applied to a substrate (i.e., they spread over the interface rather than being beaded up). Additionally, the ability of the complex coacervate to crosslink intermolecularly increases the cohesive strength of the adhesive complex coacervate. The adhesive complex coacervates have numerous biological applications as bioadhesives and drug delivery devices. In particular, the adhesive complex coacervates described herein are particularly useful in underwater applications and situations where water is present such as, for example, physiological conditions.

46 Claims, 19 Drawing Sheets

(56) References Cited

U.S. PATENT DOCUMENTS

| | | | |
|---|---|---|---|
| 2005/0020734 A1 | 1/2005 | Asgarzadeh et al. | |
| 2005/0147580 A1 | 7/2005 | Connor et al. | |
| 2005/0220751 A1 | 10/2005 | Charmot et al. | |
| 2005/0281883 A1 | 12/2005 | Daniloff et al. | |
| 2006/0007528 A1 | 1/2006 | Cao et al. | |
| 2006/0015083 A1 | 1/2006 | Munro et al. | |
| 2006/0039950 A1* | 2/2006 | Zhou et al. | 424/423 |
| 2006/0116682 A1 | 6/2006 | Longo | |
| 2006/0122290 A1* | 6/2006 | Hubbell et al. | 523/113 |
| 2006/0156954 A1 | 7/2006 | Li et al. | |
| 2006/0183848 A1 | 8/2006 | Maier et al. | |
| 2006/0240064 A9 | 10/2006 | Hunter et al. | |
| 2006/0241242 A1 | 10/2006 | Devlin | |
| 2006/0275337 A1* | 12/2006 | Cohen Stuart et al. | 424/423 |
| 2006/0276371 A1 | 12/2006 | Schreiner et al. | |
| 2007/0020469 A1* | 1/2007 | Wood et al. | 428/480 |
| 2007/0077276 A1* | 4/2007 | Haynie | 424/423 |
| 2007/0085059 A1* | 4/2007 | Mora-Gutierrez et al. | 252/400.21 |
| 2007/0191273 A1 | 8/2007 | Ambati | |
| 2007/0196454 A1 | 8/2007 | Stockman et al. | |
| 2008/0003288 A1* | 1/2008 | Bromberg et al. | 424/486 |
| 2008/0075778 A1 | 3/2008 | Heller | |
| 2009/0162407 A1 | 6/2009 | Biggs et al. | |
| 2010/0056474 A1 | 3/2010 | Baker et al. | |
| 2010/0120923 A1 | 5/2010 | Stewart et al. | |
| 2010/0291169 A1 | 11/2010 | Toreki et al. | |
| 2010/0305626 A1* | 12/2010 | Stewart et al. | 606/86 R |
| 2011/0054392 A1 | 3/2011 | Nies | |
| 2011/0287067 A1 | 11/2011 | Stewart | |
| 2011/0288274 A1 | 11/2011 | Russell et al. | |
| 2013/0129787 A1 | 5/2013 | Stewart | |
| 2013/0189313 A1 | 7/2013 | Stewart | |
| 2014/0287061 A1 | 9/2014 | Landolina | |

FOREIGN PATENT DOCUMENTS

| | | |
|---|---|---|
| CN | 101405037 | 4/2009 |
| DE | 19810965 | 9/1999 |
| EP | 0632329 | 6/1994 |
| JP | 2003280056 | 12/1991 |
| JP | 2002166158 | 6/2002 |
| JP | 2009084224 | 4/2009 |
| JP | 2009084292 | 4/2009 |
| WO | 9506056 | 3/1995 |
| WO | 02092217 | 11/2002 |
| WO | 02100453 | 12/2002 |
| WO | 2005019421 | 3/2005 |
| WO | 2007024972 | 3/2007 |
| WO | WO 2007/030811 | 3/2007 |
| WO | WO 2009/094060 | 7/2009 |
| WO | 2011011658 | 1/2011 |
| WO | 2011028967 | 3/2011 |
| WO | 2011106595 | 9/2011 |
| WO | 2011149907 | 12/2011 |
| WO | 2012065148 | 5/2012 |

OTHER PUBLICATIONS

Cement Proteing of the Tube Building Polychaete Phragmatopoma Califormica, Zhao et al., Oct. 14, 2005, The Journal of Biological Chemistry, 1-18.*
Polyethyleneimine: EPOMIN, website, Nippon Shokubai, 2014.*
Office Action issued in Russian Patent Application No. 2010135333/15(050196) dated Nov. 6, 2012.
U.S. Appl. No. 13/295,061, filed Nov. 12, 2011.
Stewart et al., "The Tube Cement of Phragmatopoma Californica: A Solid Foam." The Journal of Experimental Biology, 2004, vol. 207, No. 26, pp. 4727-4734, esp. pp. 4727-4728, 4731-4734, published online Dec. 3, 2004; <URL: http://jeb.biologists.org/cgi/reprint/207/26/4727.pdf>.
Zhao et al., "Cement Proteins of the Tube-Building Polychaete Phragmatopoma Californica." The Journal of Biological Chemistry, 2005, vol. 280, No. 52, pp. 42938-42944, esp. p. 42939-42943; table 1 Published online Oct. 14, 2005: <URL:http://www.jbc.org/cgi/reprint/280/52/42938.pdf>.
Lee et al., "Single-molecule mechanics of mussel adhesion." PNAS 2006, vol. 103, No. 35, pp. 12999-13003.
Kayitmazer et al., "Mesophase separation and probe dynamics in protein-polyelectrolyte coacervates." Soft Matter, 2007, vol. 3, pp. 1064-1076.
Lim et al., "The Adhesive Properties of Coacervated Recombinant Hybrid Mussel," Biomaterials 2010, vol. 31, No. 13, pp. 3715-3722.
Liu et al., "Chemistry of Periodate-Mediated Cross-Linking of 3,4-Dihydroxylphenylalanine-Containing Molecules to Proteins," J. Am. Chem. Soc. 2006, pp. 15228-15235.
Stevens et al., "Multiscale Structure of the Underwater Adhesive of Phragmatopoma Californica: a Nanostructured Latex with a Steep Microporosity Gradient," Langmuir 2007, 23, pp. 5045-5049.
International Search Report and Combination Written Opinion, mailed on Jan. 6, 2009 in re International Patent Application No. PCT/US2008/083311, filed on Nov. 13, 2008.
U.S. Appl. No. 12/508,280, filed Jul. 23, 2010.
Second Office Action issued in Chinese Patent Application No. 200880128307.2 dated Apr. 1, 2012, 9 pages.
International Search Report and Combination Written Opinion in re PCT/US10/43009, filed Jul. 23, 2010, mailing date Nov. 22, 2010.
PCT International Preliminary Report on Patentability for International Application No. PCT/US2008/083311, date of issuance Jul. 27, 2010, 10 pages.
Chinese First Office Action in CN Patent Application No. 200880128307.2, issued on Oct. 27, 2011, 13 pages.
Lee et al., "Synthesis of 3,4-dihydroxyphenylalanine (DOPA) containing monomers and their co-polymerization with PEG-diacrylate to form hydrogels," J. Biomater Sci. Polymer Edn., vol. 15, No. 4, pp. 449-464 (2004).
A. Basak Kayitmazer, Himadri B. Bohidar, Kevin W. Mattison, Arijit Bose, Jayashri Sarkar, Akihito Hashidzume, Paul S. Russo, Werner Jaeger, and Paul L. Dubin; "Mesophase Separation and Probe Dynamics In Protein-Polyelectrolyte Coacervates;" *Soft Matter*, 2007, 3, Published Jun. 25, 2007; pp. 1064-1076.
Supplementary Extended European Search Report for European Application No. 08871349.0 dated Nov. 14, 2011, 4 pages.
Polyethyleneimine:EPOMIN, website, Nippon Shokubai, 2014.
Canadian Office Action for Application 2,712,843 dated Jul. 9, 2014.
Chinese Office Action for Application 201080038397.3 dated Sep. 11, 2014.
Chinese Office Action for Application 2012800362923 dated Jan. 7, 2015.
Notice of Preliminary Rejection from Korean Intellectual Property Office for Application 10-2010-7018637 dated Jan. 6, 2015.
Official Action for European Application 13 156 643.2-1302 dated Dec. 22, 2014.
US Advisory Action for U.S. Appl. No. 13/580,794 dated Nov. 13, 2014.
US Office Action for U.S. Appl. No. 12/864,045 dated Jan. 5, 2015.
US Office Action for U.S. Appl. No. 13/114,397 dated Oct. 23, 2014.
US Office Action for U.S. Appl. No. 13/295,061 dated Jan. 12, 2015.
US Office Action for U.S. Appl. No. 13/617,882 dated Nov. 19, 2014.
Supplementary European Search Report for EP Application No. 12804996 dated Feb. 19, 2015.
Wang et al., "A novel bioadhesive protein of silk filaments spun underwater by caddisfly larvae", Adv. Mater. Res., 2009, vol. 79-82, pp. 1631-1634.
US Office Action for U.S. Appl. No. 13/580,794 dated May 12, 2015.
US Advisory Action for U.S. Appl. No. 13/114,397 dated Mar. 23, 2015.
US Office Action for U.S. Appl. No. 13/114,397 dated May 22, 2015.
First Examination Report for Indian Application 1584/MUMNP/2010 dated May 15, 2015.
US Office Action for U.S. Appl. No. 13/617,882 dated Jun. 15, 2015.
Mo et al., "Soft tissue adhesive composed of modified gelatin and polysaccharides," J. Biomater. Sci. Polymer Edn., 2000, vol. 11, No. 4, pp. 341-351.

(56) References Cited

OTHER PUBLICATIONS

Berg et al., "The Thermal Transition of a Non-Hydroxylated Form of Collagen. Evedence for a Role for Hydroxyproline in Stabilizing the Triple-Helix of Collagen", Biochem Biophys Res Commun, 1973, vol. 52, pp. 115-112.
Hwang et al., "Expression of Functional Recombinant Mussel Adhesive Protein Mgfp-5 in *Escherichia coli*", Applied and Environmental Microbiology, 2004, vol. 70, No. 6, pp. 3352-359.
Kamachi et al. "Synthesis of Block Polmers for Desalination Membranes. Preparation of Block Coplymers of 2-Vinylpyridine and Methacrylic Acid or Acrylic Acid", Macromolecules, 1972, vol. 5, No. 2, pp. 161-168.
Lee et al. "Rapid Gel Formation and Adhesion in Photocurable and Biodegradable Block Copolymers with High DOPA Content", Macromolecules, 2006, vol. 39, pp. 1740-1748.
Shao et al., "A Water-Borne Adhesive Modeled after the Sandcastle Glue of P. californica," Macromolecules Bioscience, vol. 9, Issue 5, Published Online Nov. 28, 2008, pp. 464-471.
Stewart et al., "The Tube Cement of Phragmatopoma Californica: A Solid Foam", The Journal of Experimental Biology, 2004, vol. 207, No. 26, pp. 4727-4734.
Yu et al., "Synthetic Polypeptide Mimics of Marine Adhesives", Macromolecules, 1998, vol. 31, pp. 4739-4745.
Chinese First Office Action in CN Patent Application 201080038397 issued Apr. 3 2013; 7 pp. (English summary).
Chinese First Office Action in CN Patent Application 201180024981.8 issued Mar. 27, 2014; 9 pp. (English summary).
Chinese First Office Action in CN Patent Application 201180050846.0 issued Apr. 3, 2014; 7 pp. (English summary).
Chinese First Office Action in CN Patent Application No. 201180010546 issued on Aug. 13, 2013 (English translation).
Chinese Second Office Action in CN Patent Application 201080038397 issued Dec. 16, 2013; 4 pp.
Chinese Second Office Action in CN Patent Application No. 201180010546 issued on Jul. 2, 2014 (English summary).
Chinese Third Office Action in CN Patent Application 201080038397 issued Aug. 21, 2014; 4 pp.
International Search Report mailed on Aug. 26, 2013 for International Application No. PCT/US2013/029131.
International Search Report mailed on May 7, 2012 for International Application No. PCT/US2011/060500.
Japanese First Office Action in JP Application No. 2012-521803 issued Aug. 6, 2014; 4 pp.
Japanese First Office Action in JP Application No. 2012-555168 issued Aug. 12, 2014; 2 pp.
PCT International Search Report for International Search Report and the Written Opinion of the International Searching Authority, or the Declaration for International Application No. PCT/US2011/0376797, mailed on Sep. 13, 2011, pp. 9.
Supplementary European Search Report for European Application No. 10802933.1 dated Jun. 24, 2014, pp. 11.
Written Opinion of the International Searching Authority issued in PCT/US2011/26169 dated May 17, 2011.
Written Opinion of the International Searching Authority issued in PCT/US2012/044299 dated Nov. 16, 2012.
US Advisory Action for U.S. Appl. No. 12/864,045 dated Sep. 23, 2014.
US Advisory Action for U.S. Appl. No. 13/617,882 dated Sep. 18, 2014.
US Office Action for U.S. Appl. No. 12/508,280 dated Sep. 20, 2011.
US Office Action for U.S. Appl. No. 12/864,045 dated Jun. 18, 2014.
US Office Action for U.S. Appl. No. 12/864,045 dated Oct. 7, 2013.
US Office Action for U.S. Appl. No. 13/114,397 dated Feb. 27, 2014.
US Office Action for U.S. Appl. No. 13/295,061 dated Mar. 4, 2014.
US Office Action for U.S. Appl. No. 13/580,794 dated Aug. 1, 2014.
US Office Action for U.S. Appl. No. 13/580,794 dated Jan. 10, 2014.
US Office Action for U.S. Appl. No. 13/617,882 dated Aug. 27, 2013.
US Office Action for U.S. Appl. No. 13/617,882 dated Jun. 5, 2014.

* cited by examiner

Pc-1:
MKVFIVLALVSAA YGCGVGIGC
AGGRCGGACG GKGYGYGG-K LGYGAYGKGG
IGGYGYGKGC VGGYGYGGLG AGK-------
LGGYGYGGSK CGGYGYGGQK LGGYGYGGKK
LGGYGYAAKK VGGYGYGAKK VGGYGYGAKK
VGGYGYGAKK VGGYGYGAKK VGGYGYGAKK
VGGYGYGAKK VGGYGYGVKK VGGYGYG---

MW = 18,240
pI = 9.74

Pc-2:
MKVLIFLATVAAVYG CGGGG WRSGSCGG
RWGHPAV----HKALGGYG-G
MGANPAVHAAVHKALGGYGAGAYGAGA
WG-HPAV----HKALGGYGAGA
WG-HPAV----HKALGGYG-G
YGAHPAVHVAVHKALGGYGAGACGHKTGGYGG
YGAHP----VAV-KA--AY-NHGFNYGANNAIKSTKRFGG
YGAHP----V-VKKAFSRGLSHGAY-AG
SKAATGYGYGSGKAAGGYGY

MW = 21,116
pI = 9.91

Pc-3A:
MKLLSVFAIVVLAVYITHVEA
DSSSSSTSSSSSYSSSSSSSSSSSSYSSSSSYSSSSSSSS
SYSSSSSYSSSSSSSYSSSSSYSSSSSYSSSSILTSTS
SSDWKRKVPARRVLRTRRFLKCVTRCTLRCTLFRSAKT
CARKCSRRCLKRVF

MW = 13,979       polyphosphoserines
pI = 2.5

Pc-3H:
MKSFTIFAAILVALCYIQISEAG
CCKRYSSSSYSSSSSSSSSSYSSSSSSSSSYSSSSSSSS
SYSSSSSSSYSSSSSSSSSYSSSSSSSSSYSSSSSSSSS
YSSSSSSSYSSSSSSYSSSSSSSSSSSSYSSSSSYSSSS
SSSSSSSYSSSSSSSSSSSYSSSSSSSSSSYSSSSSSSS
SSSSYSSSSSSSSSSSSYSSSSSSSSSSSSSSYSSSSS
SSSSYSSSSSSSSSSSSSSSSSYSSSSSSSSYSSSSYSS
SSSSYSSSSSSSSSSSSSSSSYSSSSSSSSSSSSYSS.S
SSSSSSSSSSSYSSS
MW=30,525
pI=2.5

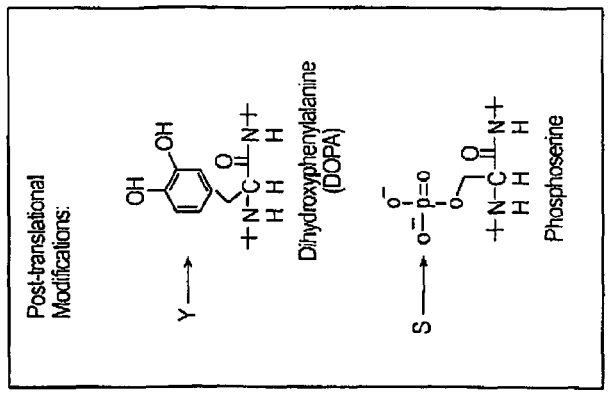

Post-translational Modifications:

Dihydroxyphenylalanine (DOPA)

Phosphoserine

FIG. 3

PC-4:
MPTLYKKVGKLVLIAIIVTVASVASA
GYPTYSPSGGTHSGYNGPHGNVVKK
TYRGPYGAGAAK
AWNGYHGAGYTSVHHGPASTSWHTS
WSNKKGGYGYGLK
---NK-GYGYGLKKVGY
-GVGL------HAAGW
HGVGPYGAGY--HGAGW
NGLGYHGAGYGV
H

Pc-4: MW = 24,330 pI = 9.49

MPTLYKKVGKLVILAIIVTVASVASA
GYPTYSPSGGTHSGYNGPHGNVVKK
TYRGPYGAGAAK
AWNGYHGAGYTSVHHGPASTSWHTS
WSNKKGGYGYGLK
---NK-GYGYGLKKVGY
-GVGL------HAAGW
HGVGPYGAGY--HGAGW
NGLGYHGAGYGV HGVGLHGAGYGL
HGVGLHGVGYL HGVGLHGAGYGL
HGVGLHGVGYGL HGVGLHGAGYGI
HGVGLHGVGYGL HGVGLHGAGYGL
HGVGLHGVGYGL HGVGLHGAGCGIHKTACY
-GVGLHG-----HY

Pc-5: MW = 14,963 pI = 8.34

MKFLVLLALVASASA
YYPLMGGF
HGGWHAPMVHGGLY
HGGWHAPMVHGGLY
HGGWHAPIV
HGGWHAPVE
----HAPAPIHTVSHSVVN
---HVPMMPM
---WHHPAPAPAPAPRP
GRIIILGGGKYGPFGKYGGG
AGLLALGALGGNGGFWKRR

Pc-6: MW = 37,763 pI = 8.25

METLFYNANFVQKSWVLILLGLAAVVA
CSEYDKGLGGYGRPSYGGRRGYGGRRGLQYHGK
YQGRCEYDGLYFRDEKSFVYCSNRNSYIQPCAP
GTRNSPYTKYNRGSKYNYRDFCEFNLVDSGYVP
KPGYLPAPKKAYPTKVYDL
KVDYAP KVDYAP KVDYAP KVDYAP
KVDYAPKASVVPPKASYVDPTPTYGYEAPFK
GGYDKPSYGKDVDTSYESKTTYTVEKTAD
KGYGKGYGDKEISAKKSYTLTEKRDYDT
GYDNSRSDEDSKEY
GYDNDRSESYERTESYTDERTDGYGTQK
VEYTQQSEYDRVTRRGIWLHKGTEVEHVLY

Pc-7: MW = 15,073 pI = 8.50

MNTFVVIAAIVAVAA
CSGGYDGRQYTYRGR
YNNKCGNDGLYFKDDKNFXFCSN
GNSYVQPCAPGTRNS
GYNNYKQGSIYNYRDFCDVNLVDE
GYGVGAKPGYNKGYNP
GYNPGYGGYNPGYST
GYGGYKAGPGPYW

Pc-8: MW = 16,772 pI = 10.29

MSNAFLXCQLCTKKLALLLLVAVCAAVAVNA
CGPLGCS GGYGGVLK
CGVGGCALGGYGGGYSAGIGGYGIK
RLGCRGGRCGLRRRVGCRGGRCGLRG
RLGCRGGRCGLR KLGCRGGRCGLRG
RLGCRGGROGLRKRLGCRGGR
GRGGYGGGYGGVCSKGVCGGYPAYGK

FIG. 5

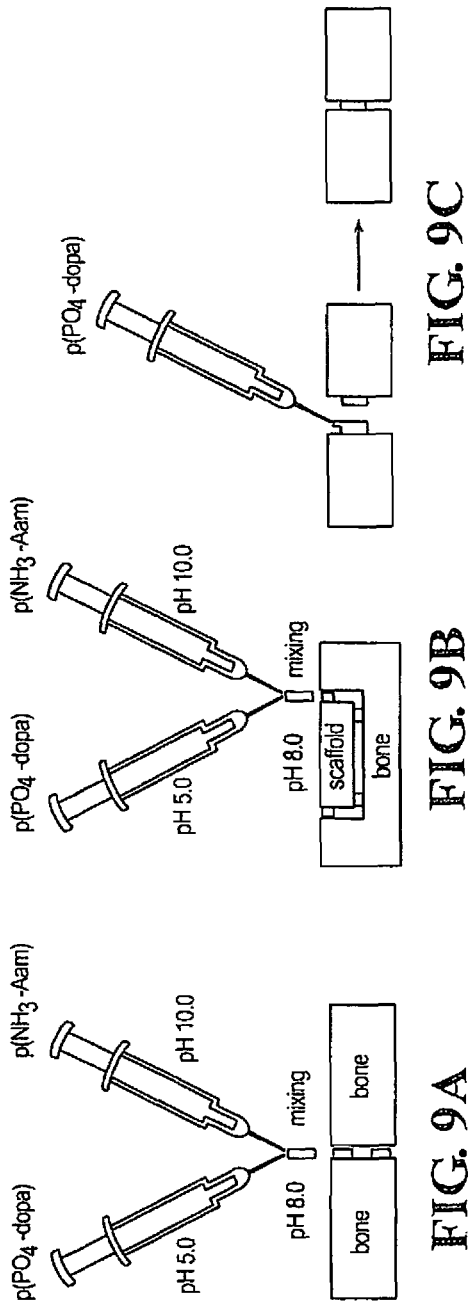

Protein Sequences
Amino Acid Mol %

| | Pc1 | Pc2 | Pc3a | Pc3b | Pc4 | Pc5 | Pc6 | Pc7 | Pc8 | Predicted* | Experimental† | |
|---|---|---|---|---|---|---|---|---|---|---|---|---|
| Ala (A) | 7.8 | 20.0 | 2.3 | 0.0 | 7.7 | 9.2 | 5.2 | 5.8 | 5.9 | 7.2 | 9.8 | |
| Arg (R) | 0.5 | 2.1 | 10.0 | 0.3 | 0.4 | 2.8 | 5.8 | 3.6 | 14.2 | 2.0 | 2.9 | (+) |
| Asn (N) | 0.0 | 2.1 | 0.0 | 0.0 | 2.4 | 1.4 | 3.0 | 11.7 | 1.2 | 1.0 | 2.8 | |
| Asp (D) | 0.0 | 0.0 | 1.5 | 0.0 | 0.0 | 0.0 | 8.2 | 5.1 | 0.0 | 0.2 | | |
| Cys (C) | 3.1 | 1.1 | 4.6 | 0.6 | 0.0 | 0.0 | 1.5 | 3.6 | 12.4 | 1.5 | 11.0.4 | N |
| Gln (Q) | 0.5 | 0.0 | 0.0 | 0.0 | 0.0 | 0.0 | 2.1 | 2.2 | 0.6 | 0.1 | 1.4 | |
| Glu (E) | 0.5 | 0.0 | 0.0 | 0.0 | 0.0 | 4.3 | 6.1 | 1.5 | 0.0 | 0.6 | | |
| Gly (G) | 41.7 | 27.4 | 0.0 | 0.0 | 33.7 | 20.6 | 9.7 | 18.2 | 32.5 | 20.0 | 26.2 | |
| His (H) | 0.0 | 8.9 | 0.0 | 0.0 | 12.6 | 11.3 | 0.9 | 0.0 | 0.0 | 5.3 | 3.5 | (+) N |
| Ile (I) | 1.6 | 0.5 | 1.5 | 0.0 | 1.6 | 2.8 | 1.2 | 1.5 | 1.2 | 1.1 | 0.6 | |
| Leu (L) | 3.6 | 3.2 | 4.6 | 0.0 | 7.7 | 5.7 | 4.2 | 2.2 | 11.8 | 3.8 | 3.4 | |
| Lys (K) | 13.5 | 6.8 | 4.6 | 0.3 | 4.1 | 2.1 | 9.4 | 5.1 | 4.7 | 4.8 | 4.4 | (+) N |
| Met (M) | 0.5 | 0.0 | 0.0 | 0.0 | 0.0 | 4.3 | 0.3 | 0.7 | 0.6 | 0.6 | | |
| Phe (F) | 0.5 | 1.6 | 2.3 | 0.0 | 0.0 | 2.8 | 1.8 | 3.6 | 0.6 | 0.9 | 1.1 | |
| Pro (P) | 0.0 | 3.7 | 0.8 | 0.0 | 2.4 | 11.3 | 6.1 | 5.8 | 1.2 | 2.5 | 2.7 | |
| Ser (S) | 1.0 | 3.7 | 51.5 | 88.1 | 3.3 | 1.4 | 20.0 | 4.4 | 2.2 | 30.0 | 28.5 | (-) |
| Thr (T) | 0.5 | 1.6 | 4.6 | 0.0 | 2.8 | 5.7 | 6.4 | 3.6 | 0.6 | 2.1 | 2.2 | |
| Trp (W) | 0.0 | 2.6 | 0.8 | 0.0 | 2.0 | 4.3 | 0.6 | 0.7 | 0.0 | 1.4 | | |
| Tyr (Y) | 17.2 | 8.9 | 7.7 | 10.7 | 10.6 | 4.3 | 13.6 | 14.6 | 4.7 | 10.3 | 6.1 | |
| Val (V) | 7.3 | 5.8 | 3.1 | 0.0 | 7.7 | 5.7 | 7.0 | 5.8 | 5.3 | 4.6 | 3.4 | |

* Predicted mol% based on one copy of each of the five proteins.
† Experimental mol% from amino acid analysis of acid hydrolyzed glue.

(+) = positive charge
(-) = negative charge
N = nucleophilic

FIG. 20

ADHESIVE COMPLEX COACERVATES AND METHODS OF MAKING AND USING THEREOF

CROSS REFERENCE TO RELATED APPLICATIONS

This application claims priority upon U.S. provisional application Ser. No. 61/023,173, filed Jan. 24, 2008. This application is hereby incorporated by reference in its entirety for all of its teachings.

BACKGROUND

Bone fractures are a serious health concern in society today. In addition to the fracture itself, a number of additional health risks are associated with the fracture. For example, intra-articular fractures are bony injuries that extend into a joint surface and fragment the cartilage surface. Fractures of the cartilage surface often lead to debilitating posttraumatic arthritis. The main determining factors in the development of posttraumatic arthritis are thought to be the amount of energy imparted at the time of injury, the patient's genetic predisposition (or lack thereof) to posttraumatic arthritis, and the accuracy and maintenance of reduction. Of the three prognostic factors, the only factor controllable by orthopedic caregivers is achievement and maintenance of reduction. Comminuted injuries of the articular surface (the cartilage) and the metaphysis (the portion of the bone immediately below the cartilage) are particularly challenging to maintain in reduced (aligned) position. This relates to the quality and type of bone in this area. It also relates to the limitations of fixation with titanium or stainless steel implants.

Currently, stainless steel and titanium implants are the primary methods of fixation, but their size and the drilling necessary to place them frequently interfere with the exact manipulation and reduction of smaller pieces of bone and cartilage. A variety of bone adhesives have been tested as alternatives to mechanical fixation. These fall into four categories: polymethylmethacrylates (PMMA), fibrin-based glues, calcium phosphate (CP) cements, and CP resin composites. PMMA cements, which are used in the fixation of protheses, have well-known drawbacks, one of the most serious being that the heat generated from the exothermic setting reaction can kill adjacent bone tissue. Also, the poor bonding to bone leads to aseptic loosening, the major cause of PMMA cemented prothesis failure.

Fibrin glues, based on the blood clotting protein fibrinogen, have been tested for fixing bone grafts and repairing cartilage since the 1970s and yet have not been widely deployed. One of the drawbacks of fibrin glues is that they are manufactured from pooled human donor blood. As such, they carry risk of transmitting infections and could potentially be of limited supply.

CP cements are powders of one or more forms of CP, e.g., tetracalcium phosphate, dicalcium phosphate anhydride, and β-tricalcium phosphate. When the powder is mixed with water it forms a paste that sets up and hardens through the entanglement of one or more forms of CP crystals, including hydroxyapatite. Advantages of CP cements include isothermal set, proven biocompatibility, osteoconductivity, and they serve as a reservoir for Ca and $PO_4$ for hydroxyapatite formation during healing. The primary disadvantages are that CP cements are brittle, have low mechanical strength and are therefore not ideal for stable reduction of small articular segments. CP cements are used mostly as bone void fillers. The poor mechanical properties of CP cements have led to composite cements of CP particles and polymers. By varying the volume fractions of the particulate phase and the polymer phase, the modulus and strength of the glue can be adjusted toward those of natural bone, an avenue that is also open to us.

Given the overall health impact associated with bone fractures and the imperfect state of current fixation methods, new fixation methods are needed.

SUMMARY

Described herein is the synthesis of adhesive complex coacervates. The adhesive complex coacervates are composed of a mixture of one or more polycations, one or more polyanions, and one of more multivalent cations. The polycations and polyanions are crosslinked with one another by covalent bonds upon curing. The adhesive complex coacervates have several desirable features when compared to conventional adhesives, which are effective in water-based applications. The adhesive complex coacervates described herein exhibit low interfacial tension in water when applied to a substrate (i.e., they spread over the interface rather than being beaded up). Additionally, the ability of the complex coacervate to crosslink intermolecularly increases the cohesive strength of the adhesive complex coacervate. The adhesive complex coacervates have numerous biological applications as bioadhesives and drug delivery devices. In particular, the adhesive complex coacervates described herein are particularly useful in underwater applications and situations where water is present such as, for example, physiological conditions.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 2-7 shows several protein sequences produced by *P. californica* that can be used as polycations and polyanions in the present invention as well as synthetic polycations and polyanions useful in the present invention.

FIG. 9 shows dual syringe systems for applying small "spot welds" of complex coacervates described herein to repair fractures (A), small bone injuries (B), or bonding synthetic scaffolds to bony tissue (C).

FIG. 12 shows the liquid character of an adhesive complex coacervate. The solution of 1 and 2 contained equal quantities of amine and phosphate sidechains, pH 7.4.

DETAILED DESCRIPTION

Figure 1:
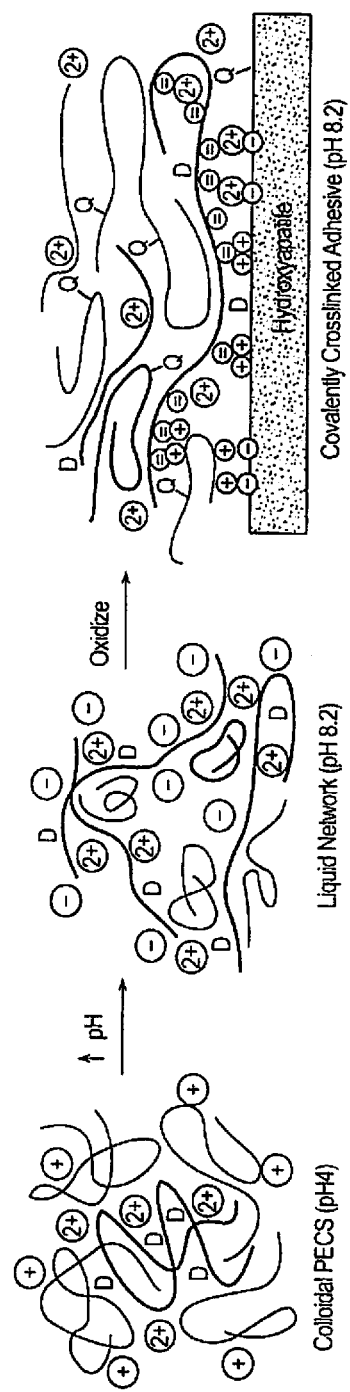
FIG. 1 shows a model of pH dependent coacervate structure and adhesive mechanisms. (A) The polyphosphate (black) with low charge density paired with the polyamine (red) form nm-scale complexes. The complexes have a net positive charge. (B) Extended high charge density polyphosphates form a network connected by more compact lower charge density polyamines and when present divalent cations (green symbols). The net charge on the copolymers is negative. (C) Oxidation of 3,4-dihydroxyphenol (D) by $O_2$ or an added oxidant initiates crosslinking between the quinone (Q) and primary amine sidechains. The coacervate can adhere to the hydroxyapatite surface through electrostatic interactions, 3,4-dihydroxyphenol sidechains, and quinone-mediated covalent coupling to matrix proteins.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$, $R^2$, $R^3$, $R^4$, $R^5$, X, m, and n used throughout the application are the same variables as previously defined unless stated to the contrary.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

Any of the compounds described herein can be the pharmaceutically-acceptable salt. In one aspect, pharmaceutically-acceptable salts are prepared by treating the free acid with an appropriate amount of a pharmaceutically-acceptable base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

In another aspect, if the compound possesses a basic group, it can be protonated with an acid such as, for example, HCl, HBr, or $H_2SO_4$, to produce the cationic salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

Described herein are adhesive complex coacervates and their applications thereof. In general, the complexes are a mixture of cations and anions in balanced proportions to produce stable aqueous complexes at a desired pH. The adhesive complex coacervate comprises at least one polycation, at least one polyanion, and at least one multivalent cation, wherein at least one polycation or polyanion is a synthetic compound, and the polycation and/or polyanion are crosslinked with one another upon curing the complex coacervate. Each component of the coacervate and methods for making the same are described below.

The adhesive complex coacervate is an associative liquid with a dynamic structure in which the individual polymer components diffuse throughout the entire phase. Complex coacervates behave rheologically like viscous particle dispersions rather than a viscoelastic polymer solution. As described above, the adhesive complex coacervates exhibit low interfacial tension in water when applied to substrates either under water or that are wet. In other words, the complex coacervate spreads evenly over the interface rather than being beading up. Additionally, upon intermolecular crosslinking, the adhesive complex coacervate forms a strong, insoluble, cohesive material.

Conversely, polyelectrolyte complexes (PECs), which can be a precursor to the adhesive complex coacervates described herein, are small colloidal particles. For example, referring to FIG. 11A, a solution of PECs at pH 3.1 and 4.2 exists as a milky solution of colloidal particles having a diameter of about 300 nm Upon raising the pH to 7.2 and 8.1, the PEC condenses into a liquid phase of concentrated polymers (the coacervate phase) and a dilute equilibrium phase. In this aspect, the PEC can be converted to an adhesive complex coacervate described herein.

An exemplary model of the differences in phase behavior between the polyelectrolyte complex and the adhesive complex coacervate is presented in FIG. 1. At low pH the oppositely charged polyelectrolytes associate electrostatically into nano-complexes with a net positive surface charge that stabilizes the suspension to produce PEC 1. With increasing pH the net charge of the complexes changes from positive to negative but remains near net neutrality. The PEC can form a loose precipitate phase, which can be converted to a complex coacervate 2 by raising the pH further (FIG. 1). Thus, in certain aspects, the conversion of the PEC to complex coacervate can be "triggered" by adjusting the pH and/or the concentration of the multivalent cation. For example, the PEC can be produced at a pH of less than or equal to 4, and the pH of the PEC can be raised to greater than or equal to 7.0, from 7.0 to 9.0, or from 8.0 to 9.0 to convert the PEC to a complex coacervate. Subsequent crosslinking between the polycation and polyanions (e.g., oxidation and covalent crosslinking as shown in FIG. 1C) results in the formation of the adhesive complex coacervate described herein.

The polycations and polyanions contain groups that permit crosslinking between the two polymers upon curing to produce new covalent bonds and the adhesive complex coacervate described herein. The mechanism of crosslinking can vary depending upon the selection of the crosslinking groups. In one aspect, the crosslinking groups can be electrophiles and nucleophiles. For example, the polyanion can have one or more electrophilic groups, and the polycations can have one or more nucleophilic groups capable of reacting with the electrophilic groups to produce new covalent bonds. Examples of electrophilic groups include, but are not limited to, anhydride groups, esters, ketones, lactams (e.g., maleimides and succinimides), lactones, epoxide groups, isocyanate groups, and aldehydes. Examples of nucleophilic groups are presented below.

In one aspect, the crosslinkable group includes a hydroxyl-substituted aromatic group capable of undergoing oxidation in the presence of an oxidant. In one aspect, the hydroxyl-substituted aromatic group is a dihydroxyphenol or halogenated dihydroxyphenol group such as, for example, DOPA and catechol (3,4 dihydroxyphenol). For example, in the case of DOPA, it can be oxidized to dopaquinone. Dopaquinone is an electrophilic group that is capable of either reating with a neighboring DOPA group or another nucleophilic group. In the presence of an oxidant such as oxygen or other additives including, but not limited to, peroxides, periodates, or transition metal oxidants (e.g., $NaIO_4$ or a $Fe^{+3}$ compound), the hydroxyl-substituted aromatic group can be oxidized. In another aspect, crosslinking can occur between the polycation and polyanion via light activated crosslinking through azido groups. Once again, new covalent bonds are formed during this type of crosslinking.

Figure 8:
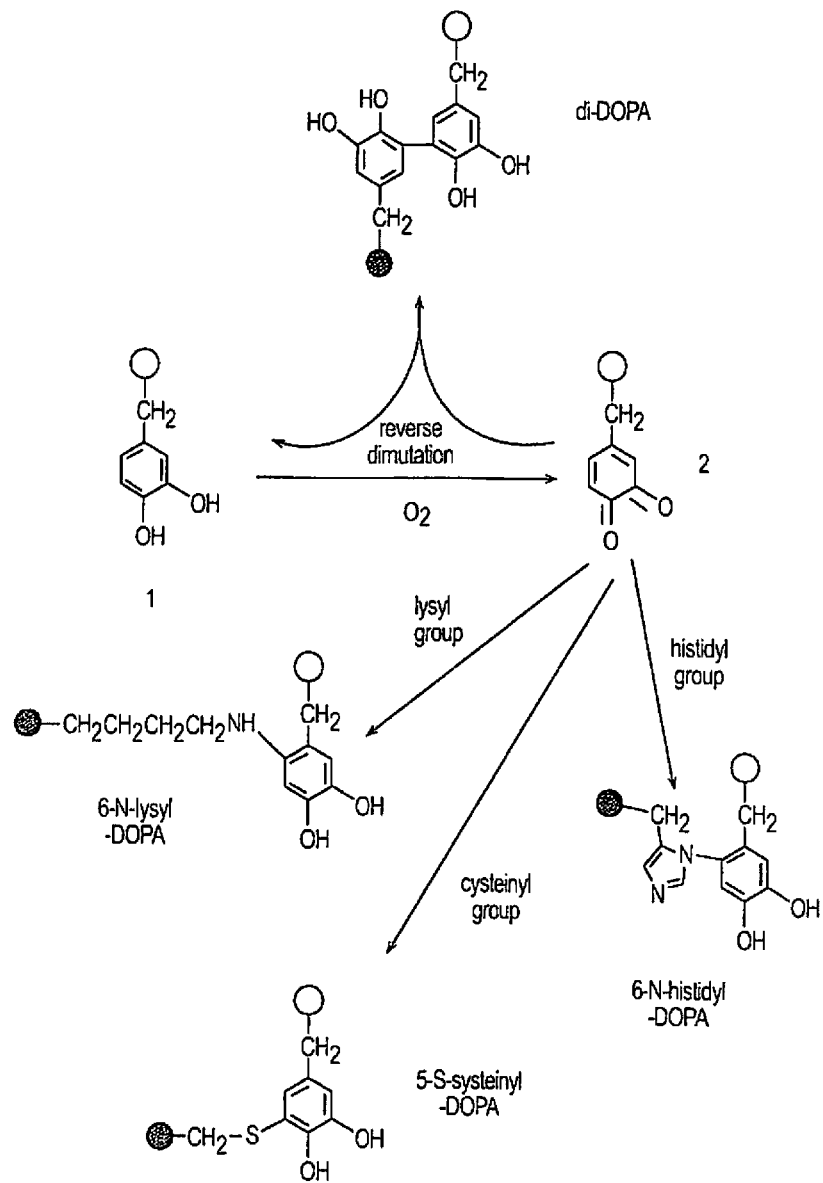
FIG. 8 shows different mechanisms of DOPA crosslinking.

The stability of the oxidized crosslinker can vary. For example, the phosphono containing polyanions described herein that contain oxidizable crosslinkers are stable in solution and do not crosslink with themselves. This permits nucleophilic groups present on the polycation to react with the oxidized crosslinker. This is a desirable feature of the invention, which permits the formation of intermolecular bonds and, ultimately, the formation of a strong adhesive. Examples of nucleophilic groups that are useful include, but are not limited to, hydroxyl, thiol, and nitrogen containing groups such as substituted or unsubstituted amino groups and imidazole groups. For example, residues of lysine, histidine, and/or cysteine can be incorporated into the polycation and introduce nucleophilic groups. An example of this is shown in FIG. 8. DOPA residue 1 can be oxidized to form a dopaquinone residue 2. Dopaquinone is a reactive intermediate and can crosslink (i.e., react) with a DOPA residue on another polymer or the same polymer to produce a di-DOPA group. Alternatively, the dopaquinone residue can react with nucleophiles such as, for example, amino, hydroxyl, or thiol groups via a Michael-type addition to form a new covalent bond. Referring to FIG. 8, a lysyl group, cysteinyl group, and histidyl group react with the dopaquinone residue to produce new covalent bonds. Although DOPA is a suitable crosslinking group, other groups such as, for example, tyrosine can be used herein. The importance of crosslinking with respect to the use of the adhesive complex coacervates described herein will be discussed below.

In other aspects, the crosslinkers present on the polycation and/or polyanion can form coordination complexes with transition metal ions. For example, a transition metal ion can be added to a mixture of polycation and polyanion, where both polymers contain crosslinkers capable of coordinating with the transition metal ion. The rate of coordination and dissociation can be controlled by the selection of the crosslinker, the transition metal ion, and the pH. Thus, in addition to covalent crosslinking as described above, crosslinking can occur through electrostatic, ionic, or other non-covalent bonding. Transition metal ions such as, for example, iron, copper, vanadium, zinc, and nickel can be used herein.

The polycation and polyanion are generally composed of a polymer backbone with a plurality of chargeable groups at a particular pH. The groups can be pendant to the polymer backbone and/or incorporated within the polymer backbone. The polycation is any biocompatible polymer possessing cationic groups or groups that can be readily converted to cationic groups by adjusting the pH. In one aspect, the polycation is a polyamino compound. The amino group can be branched or part of the polymer backbone. The amino group can be a primary, secondary, or tertiary amino group that can be protonated to produce a cationic ammonium group at a selected pH. For example, the amino group can be derived from a residue of lysine, histidine, or imidazole attached to the polycation. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate and methylsulfate.

The polycation can be a synthetic polymer or naturally-occurring (i.e., produced from organisms). In one aspect, when the polycation is naturally-occurring, the polycation is a positively-charged protein produced from *P. californica*. FIGS. 2-6 show the protein sequences of several cement proteins produced by *P. californica* (Zhao et al. "Cement Proteins of the tube building polychaete *Phragmatopoma californica*" *J. Biol. Chem.* (2005) 280: 42938-42944). Table 1 provides the amino acid mole % of each protein. Referring to FIGS. 2-5, Pc1, Pc2, and Pc4-Pc8 are polycations, where the polymers are cationic at neutral pH. The type and number of amino acids present in the protein can vary in order to achieve the desired solution properties. For example, referring to Table 1, Pc1 is enriched with lysine (13.5 mole %) while Pc4 and Pc5 are enriched with histidine (12.6 and 11.3 mole %, respectively).

In the case when the polycation is a synthetic polymer, a variety of different polymers can be used; however, it is desirable that the polymer be biocompatible and non-toxic to cells and tissue. In one aspect, the polycation includes a polyacrylate having one or more pendant amino groups. For example, the backbone can be a homopolymer or copolymer derived from the polymerization of acrylate monomers including, but not limited to, acrylates, methacrylates, acrylamides, and the like. In one aspect, the backbone of the polycation is polyacrylamide. In other aspects, the polycation is a block co-polymer, where segments or portions of the co-polymer possess cationic groups depending upon the selection of the monomers used to produce the co-polymer.

In one aspect, the polycation is a polyamino compound. In another aspect, the polyamino compound has 10 to 90 mole % tertiary amino groups. In a further aspect, the polycation polymer has at least one fragment of the formula I

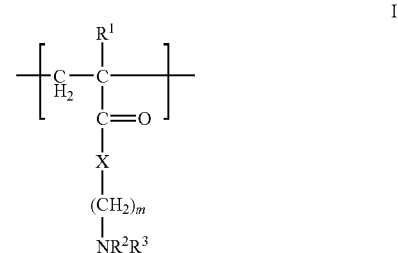

wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula I, the polymer backbone is composed of —$CH_2$—$C(R^1)$—$C(O)X$—, which is a residue of an acrylate, methacrylate, acrylamide, or methacrylamide. The remaining portion of formula I $(CH_2)_m$—$NR^2R^3$ is the pendant amino group. FIG. 3 (structures C and D) and FIG. 6 (4 and 7) show examples of polycations having the fragment of formula I, where the polymer backbone is composed acrylamide and methacrylate residues. In one aspect, the polycation is the free radical polymerization product of a cationic tertiary amine monomer (2-dimethylaminoethyl methacrylate) and acrylamide, where the molecular weight is from 10 to 20 kd and possesses tertiary monomer concentrations from 15 to 30 mol %. FIG. 4 (structures E and F) and FIG. 6 (5) provide examples of polycations useful herein, where imidazole groups are directly attached to the polymer backbone (structure F) or indirectly attached to the polymer backbone via a linker (structure E via a methylene linker).

Figure 2:
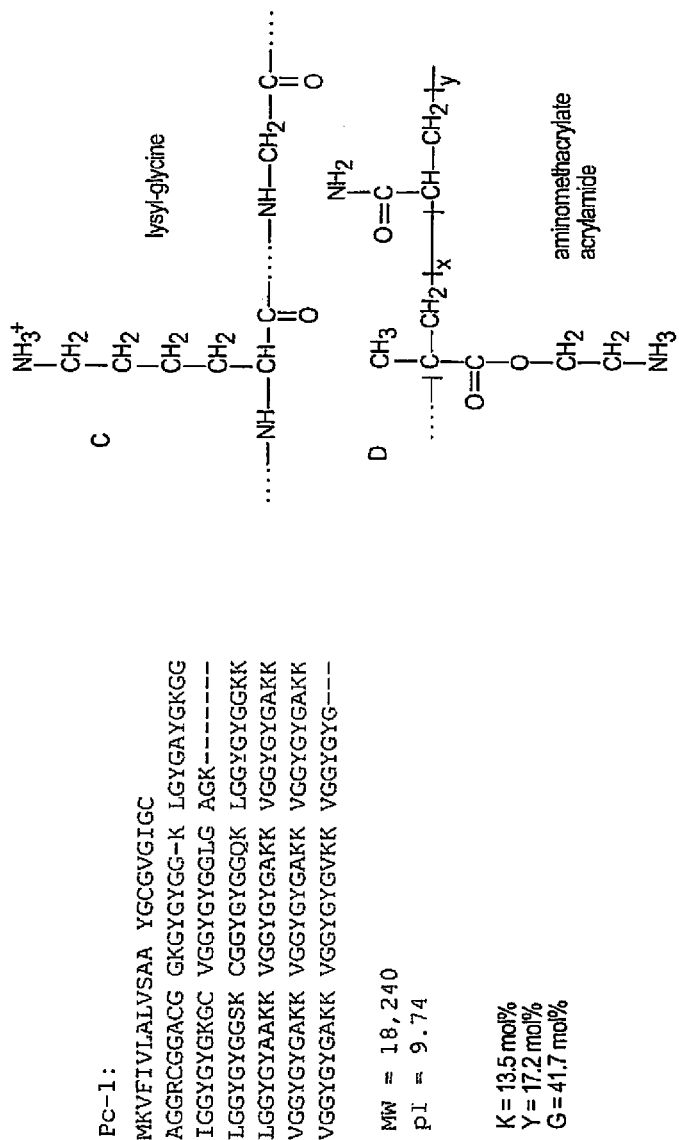
Figure 7:
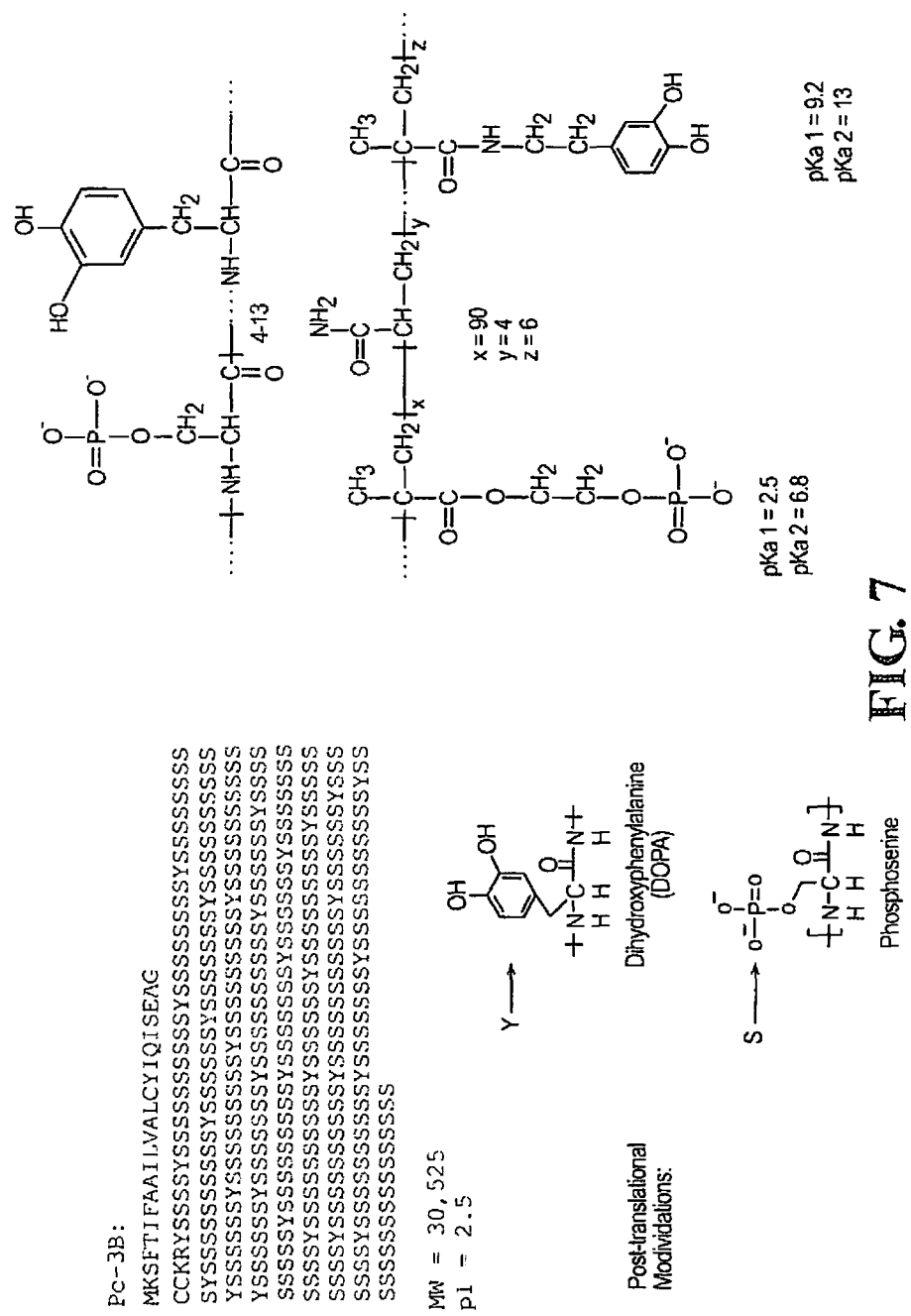

Similar to the polycation, the polyanion can be a synthetic polymer or naturally-occurring. In one aspect, when the polyanion is naturally-occurring, the polyanion is a negatively-charged protein produced from *P. californica*. FIGS. 2 and 7 show the sequences of two proteins (Pc3a and Pc3b) produced by *P. californica* (Zhao et al. "Cement Proteins of the tube building polychaete *Phragmatopoma californica*" *J. Biol. Chem.* (2005) 280: 42938-42944). Referring to Table 1, Pc3a and Pc3b are essentially composed of polyphosphoserine, which is anionic at neutral pH.

When the polyanion is a synthetic polymer, it is generally any biocompatible polymer possessing anionic groups or groups that can be readily converted to anionic groups by adjusting the pH. Examples of groups that can be converted to anionic groups include, but are not limited to, carboxylate, sulfonate, phosphonate, boronate, sulfate, borate, or phosphate. Any cationic counterions can be used in association with the anionic polymers if the considerations discussed above are met.

In one aspect, the polyanion is a polyphosphate. In another aspect, the polyanion is a polyphosphate compound having from 10 to 90 mole % phosphate groups. In a further aspect, the polyanion includes a polyacrylate having one or more pendant phosphate groups. For example, the backbone can be a homopolymer or copolymer derived from the polymerization of acrylate monomers including, but not limited to, acrylates, methacrylates, acrylamides, and the like. In one aspect, the backbone of the polyanion is polyacrylamide. In other aspects, the polyanion is a block co-polymer, where segments or portions of the co-polymer possess anionic groups depending upon the selection of the monomers used to produce the co-polymer. In a further aspect, the polyanion can be heparin sulfate, hyaluronic acid, chitosan, and other biocompatible and biodegradable polymers typically used in the art.

In one aspect, the polyanion is a polyphosphate. In another aspect, the polyanion is a polymer having at least one fragment having the formula II

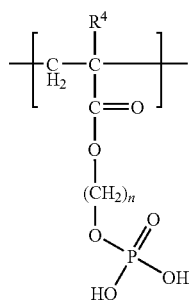

wherein $R^4$ is hydrogen or an alkyl group, and n is from 1 to 10, or the pharmaceutically-acceptable salt thereof. In another aspect, wherein $R^4$ is methyl and n is 2. Similar to formula I, the polymer backbone of formula II is composed of a residue of an acrylate or methacrylate. The remaining portion of formula II is the pendant phosphate group. FIG. 7 (structure B), shows an example of a polyanion useful herein that has the fragment of formula II, where the polymer backbone is composed acrylamide and methacrylate residues. In one aspect, the polyanion is the polymerization product ethylene glycol methacrylate phosphate and acrylamide, where the molecular weight is from 10,000 to 50,000, preferably 30,000, and has phosphate groups in the amount of 45 to 90 mol %.

Figures 6A, 6B, 6C, 6D:
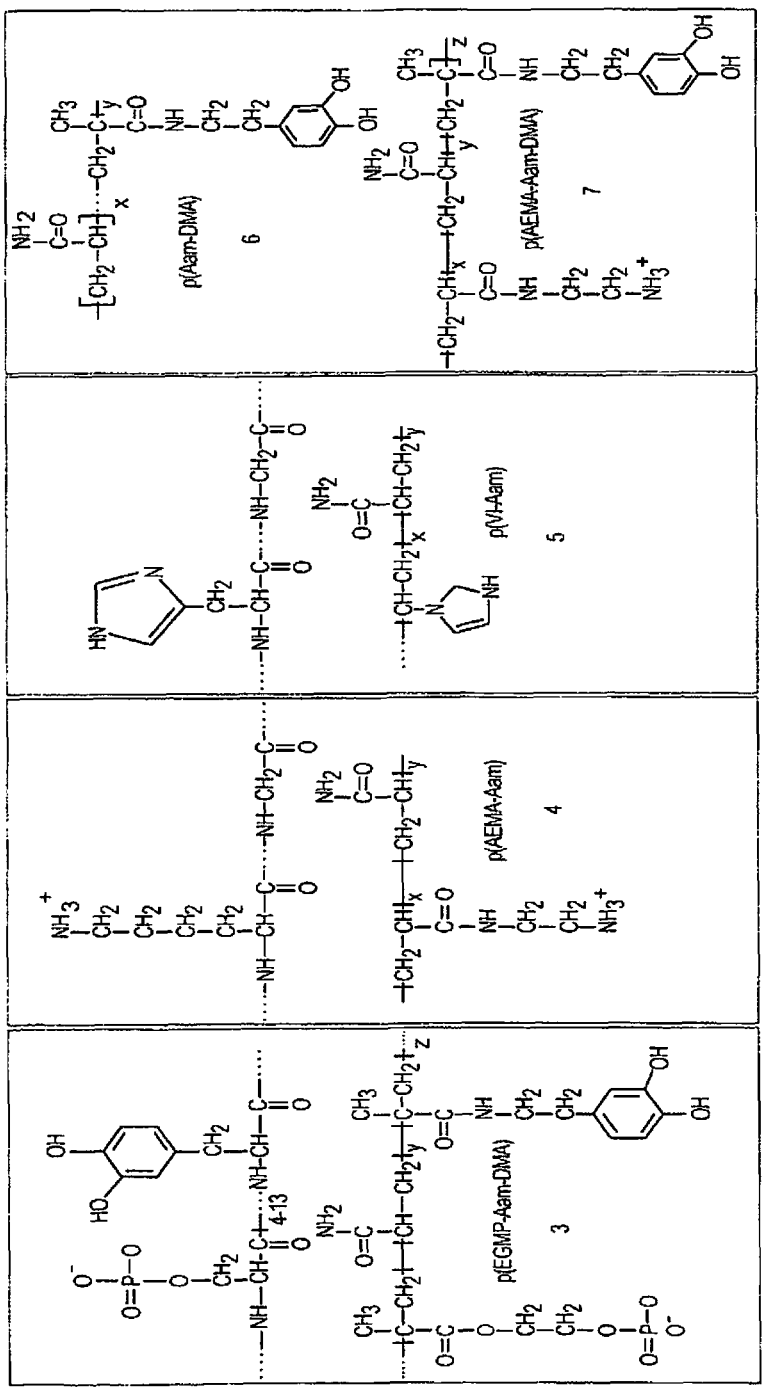

As described above, the polycation and polyanion contain crosslinkable groups. For example, the polyanion can include one or more groups that can undergo oxidation, and the polycation contains on or more nucleophiles that can react with the oxidized crosslinker to produce new covalent bonds. Polymers 3 and 7 in FIG. 6 provide examples of DOPA residues incorporated into a polyanion and polycation, respectively. In each of these polymers, an acrylate containing the pendant DOPA residue is polymerized with the appropriate monomers to produce the polyanion 3 and polycation 7 with pendant DOPA residues.

It is contemplated that the polycation can be a naturally occurring compound (e.g., protein from *P. californica*) and the polyanion is a synthetic compound. In another aspect, the polycation can be a synthetic compound and the polyanion is a naturally occurring compound (e.g., protein from *P. californica*). In a further aspect, both the polyanion and polycation are synthetic compounds.

The adhesive complex coacervates also contain one or more multivalent cations (i.e., cations having a charge of +2 or greater). In one aspect, the multivalent cation can be a divalent cation composed of one or more alkaline earth metals. For example, the divalent cation can be a mixture of $Ca^{+2}$ and $Mg^{+2}$. In other aspects, transition metal ions with a charge of +2 or greater can be used as the multivalent cation. In addition to the pH, the concentration of the multivalent cations can determine the rate and extent of coacervate formation. Not wishing to be bound by theory, weak cohesive forces between particles in the fluid may be mediated by multivalent cations bridging excess negative surface charges. The amount of multivalent cation used herein can vary. In one aspect, the amount is based upon the number of anionic groups and cationic groups present in the polyanion and polycation. In the Examples, the selection of the amount of multivalent cations with respect to producing adhesive complex coacervates and other physical states is addressed.

The adhesive complex coacervate can be synthesized a number of different ways. In one aspect, the polycation, the polyanion, and at least one multivalent cation, can be mixed with one another to produce the adhesive complex coacervate. By adding the appropriate amount of multivalent cation to the mixture of polyanion and polycation, the adhesive complex coacervate can be produced. In another aspect, the adhesive complex coacervate can be produced by the process comprising:

(a) preparing a polyelectrolyte complex comprising admixing at least one polycation, at least one polyanion, and at least one multivalent cation, wherein at least one polycation or polyanion is a synthetic compound, and the polycation and/or polyanion comprises at least one group capable of crosslinking with each other; and (b) adjusting the pH of the polyelectrolyte complex, the concentration of at least one multivalent cation, or a combination thereof to produce the adhesive complex coacervate.

In this aspect, the polyelectrolyte complex is converted to the adhesive complex coacervate. Methods for producing the adhesive complex coacervate in situ are described below.

The adhesive complex coacervates described herein have numerous benefits with respect to their use as biological cements and delivery devices. For example, the coacervates have low initial viscosity, specific gravity greater than one, and being mostly water by weight, low interfacial tension in an aqueous environment, all of which contribute to their ability to adhere to a wet surface. An additional advantage with respect to the bonding mechanism (i.e., crosslinking) of the adhesive complex coacervates includes low heat production during setting, which prevents damage to living tissue. The components can be pre-polymerized in order to avoid heat generation by in situ exothermic polymerization. This is due for the most part by the ability of the adhesive complex coacervates to crosslink intermolecularly under very mild conditions as described above.

The adhesive complex coacervates described herein can be applied to a number of different biological substrates. The substrate can be contacted in vitro or in vivo. The rate of crosslinking within the adhesive complex coacervate can be controlled by for example pH and the presence of an oxidant or other agents that facilitate crosslinking. One approach for applying the adhesive complex coacervate to the substrate can be found in FIG. 9. The techniques depicted in FIG. 9 are referred to herein as "spot welding," where the adhesive complex coacervate is applied at distinct and specific regions of the substrate. In one aspect, the adhesive complex coacervate can be produced in situ. Referring to FIG. 9A, a pre-formed stable PEC solution 1 composed of polycations and polyanions at low pH (e.g., 5) is simultaneously applied to a substrate with a curing solution 2 composed of an oxidant at a higher pH (e.g., 10) with the use of syringes. Upon mixing, the curing solution simultaneously produces the adhesive complex coacervate by crosslinking the polymers on the surface of the substrate.

In another aspect, referring to FIG. 9B, a solution of polyanions 3 and polycations 4 are applied simultaneously to the substrate. One of the solutions has a pH higher than the other in order to produce the adhesive complex coacervate. Referring to FIG. 9B, polyanion 3 is at a lower pH than the polycation solution 4; however, it is also contemplated that the polyanion can be in solution having a higher pH than the polycation. The solution having the higher pH can include an oxidant in order to facilitate crosslinking.

FIG. 9C depicts another aspect of spot welding. In this aspect, the substrate is primed with polycation at a particular pH. Next, a solution of the polyanion at a higher pH is applied to the polycation in order to produce the adhesive complex coacervate in situ. It is also contemplated that the substrate can be primed with polyanion first followed by polycation. An oxidant can then be applied separately on the complex coacervate to facilitate crosslinking to produce the adhesive complex coacervate. Alternatively, the solution applied after the substrate has been primed can contain the oxidant so that the adhesive complex coacervate is formed and subsequently crosslinked in situ.

The adhesive complex coacervates described herein can be used to repair a number of different bone fractures and breaks. The coacervates adhere to bone (and other minerals) through several mechanisms (see FIG. 1C). The surface of the bone's hydroxyapatite mineral phase ($Ca_5(PO_4)_3(OH)$) is an array of both positive and negative charges. The negative groups present on the polyanion (e.g., phosphate groups) can interact directly with the positive surface charges or it can be bridged to the negative surface charges through the cationic groups on the polycation and/or multivalent cations. Likewise, direct interaction of the polycation with the negative surface charges would contribute to adhesion. Additionally, when the polycation and/or polyanion contain catechol moieties, they can facilitate the adhesion of the coacervate to readily wet hydroxyapatite. Other adhesion mechanisms include direct bonding of unoxidized crosslinker (e.g., DOPA or other catechols) to hydroxyapatite. Alternatively, oxidized crosslinkers can couple to nucleophilic sidechains of bone matrix proteins.

Examples of such breaks include a complete fracture, an incomplete fracture, a linear fracture, a transverse fracture, an oblique fracture, a compression fracture, a spiral fracture, a comminuted fracture, a compacted fracture, or an open fracture. In one aspect, the fracture is an intra-articular fracture or a craniofacial bone fracture. Fractures such as intra-articular fractures are bony injuries that extend into and fragment the cartilage surface. The adhesive complex coacervates may aid in the maintenance of the reduction of such fractures, allow less invasive surgery, reduce operating room time, reduce costs, and provide a better outcome by reducing the risk of post-traumatic arthritis.

In other aspects, the adhesive complex coacervates described herein can be used to join small fragments of highly comminuted fractures. In this aspect, small pieces of fractured bone can be adhered to an existing bone. It is especially challenging to maintain reduction of the small fragments by drilling them with mechanical fixators. The smaller and greater number of fragments the greater the problem. In one aspect, the adhesive complex coacervate or precursor thereof may be injected in small volumes to create spot welds as described above in order to fix the fracture rather than filling the entire crack. The small biocompatible spot welds would minimize interference with healing of the surrounding tissue and would not necessarily have to be biodegradable. In this respect it would be similar to permanently implanted hardware.

In other aspects, the adhesive complex coacervates can be used to secure scaffolds to bone and other tissues such as, for example, cartilage, ligaments, tendons, soft tissues, organs, and synthetic derivatives of these materials. Using the complexes and spot welding techniques described herein, the development of scaffolds is contemplated. Small adhesive tacks composed of the adhesive complex coacervates described herein would not interfere with migration of cells or transport of small molecules into or out of the scaffold. In certain aspects, the scaffold can contain one or more drugs that facilitate growth or repair of the bone and tissue. For example, the scaffold can be coated with the drug or, in the alternative, the drug can be incorporated within the scaffold so that the drug elutes from the scaffold over time.

The adhesive complex coacervates and methods described herein have numerous dental applications. For example, the adhesive complex coacervates can be used to repair breaks or cracks in teeth, for securing crowns, or seating implants and dentures. Using the spot weld techniques described herein, the adhesive complex coacervate or precursor thereof can be applied to a specific points in the mouth (e.g., jaw, sections of a tooth) followed by attaching the implant to the substrate.

In other aspects, the adhesive complex coacervates can adhere a metal substrate to bone. For example, implants made from titanium oxide, stainless steel, or other metals are commonly used to repair fractured bones. The adhesive complex coacervate or a precursor thereof can be applied to the metal substrate, the bone, or both prior to adhering the substrate to the bone. In certain aspects, the crosslinking group present on the polycation or polyanion can form a strong bond with titanium oxide. For example, it has been shown that DOPA can strongly bind to wet titanium oxide surfaces (Lee et al., PNAS 103:12999 (2006)). Thus, in addition to bonding bone fragments, the adhesive complex coacervates described herein can facilitate the bonding of metal substrates to bone, which can facilitate bone repair and recovery.

It is also contemplated that the adhesive complex coacervates described herein can encapsulate one or more bioactive agents. The bioactive agents can be any drug that will facilitate bone growth and repair when the complex is applied to the bone. The rate of release can be controlled by the selection of the materials used to prepare the complex as well as the charge of the bioactive agent if the agent is a salt.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Mimetic Copolymer Synthesis and Characterization.

Pc3 Analogs.

The dopa analog monomer (dopamine methacrylamide, DMA) was prepared by slight modification of a published procedure. (Lee B P, Huang K, Nunalee F N, Shull K R, Messersmith P B. Synthesis of 3,4-dihydroxyphenylalanine (DOPA) containing monomers and their co-polymerization with PEG-diacrylate to form hydrogels. J Biomater Sci Polym Ed 2004; 15(4):449-464). Briefly, a borate-dopamine complex was reacted at pH>9 with methacryloyl chloride. After disrupting the borate-catechol bond by acidification, the product was washed with ethyl acetate, recrystallized from hexane, and verified by $^1$H NMR (400 MHz, DMSO-TMS): d8.8-8.58 (2H, (OH)$_2$—Ar—), 7.92 (1H, —C(=O)—NH—), 6.64-6.57 (2H, C$_6$H$_2$(OH)$_2$—), 6.42 (1H, C$_6$H$_2$H(OH)$_2$—), 5.61 (1H, —C(=O)—C(—CH$_3$)=CHH), 5.30 (1H, —C(=O)—C(—CH$_3$)=CHH), 3.21 (2H, C$_6$H$_3$(OH)$_2$—CH$_2$—CH$_2$(NH)—C(=O)—), 2.55 (2H, C$_6$H$_3$(OH)$_2$—CH$_2$—CH$_2$(NH)—C(=O)—), 1.84 (3H, —C(=O)—C(—CH$_3$)=CH$_2$).

Figure 10A:
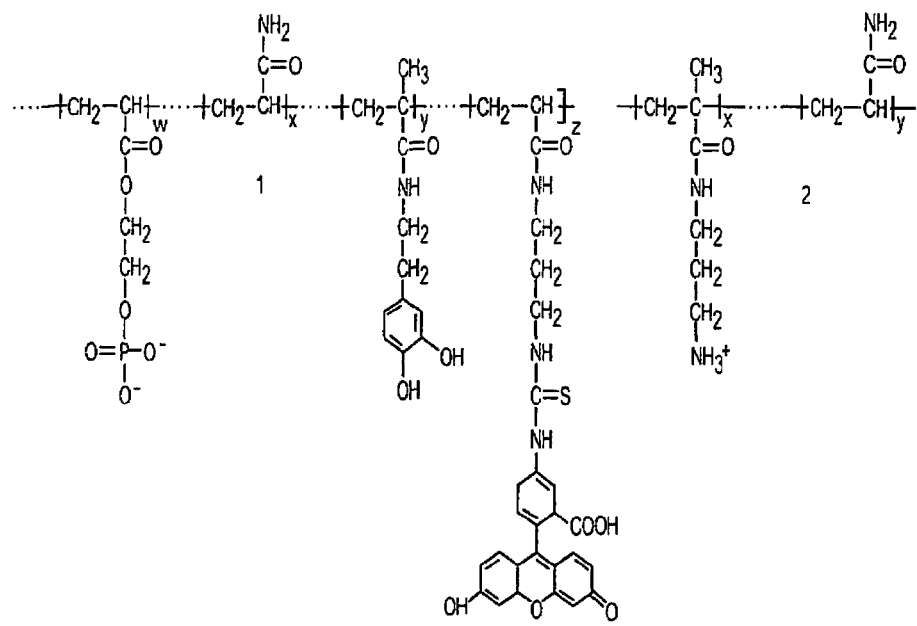
FIG. 10 shows the structure and UV/VIS characterization of mimetic copolymers. (A) The Pc3 analog, 1, contained 88.4 mol % phosphate, 9.7 mol % dopamide, and 0.1 mol % FITC sidechains. The Pc1 analog, 2, contained 8.1 mol % amine sidechains. The balance was acrylamide subunits in both cases. (B) A single peak at 280 nm characteristic of the catechol form of 3,4-dihydroxyphenol was present in the spectrum of 1. Following oxidation with $NaIO_4$ a peak at 395 nm corresponding to the quinone form appeared confirming the expected redox behavior of the 3,4-dihydroxyphenol containing polymer.

Before polymerization monoacryloxyethyl phosphate (MAEP, Polysciences) was diluted in MeOH and extracted with hexane to remove dienes. Copolymer 1 was prepared by mixing 90 mol % MAEP, 8 mol % DMA, 2 mol % acrylamide (Aam, Polysciences), and 0.1 mol % FITC-methacrylamide in MeOH at a final monomer concentration of 5 wt %. Free radical polymerization was initiated with azobisisobutyronitrile (AIBN) and proceeded at 60° C. for 24 hrs in sealed ampules. A similar procedure was used to make polymers 3-7 as shown in FIGS. 2-7. Copolymer 1 (FIG. 10) was recovered by size exclusion chromatography (SEC) in MeOH on a Sephadex LH-20 column (Sigma-Aldrich), concentrated by rotary evaporation, dissolved in DI water, and freeze dried.

Figure 10B:
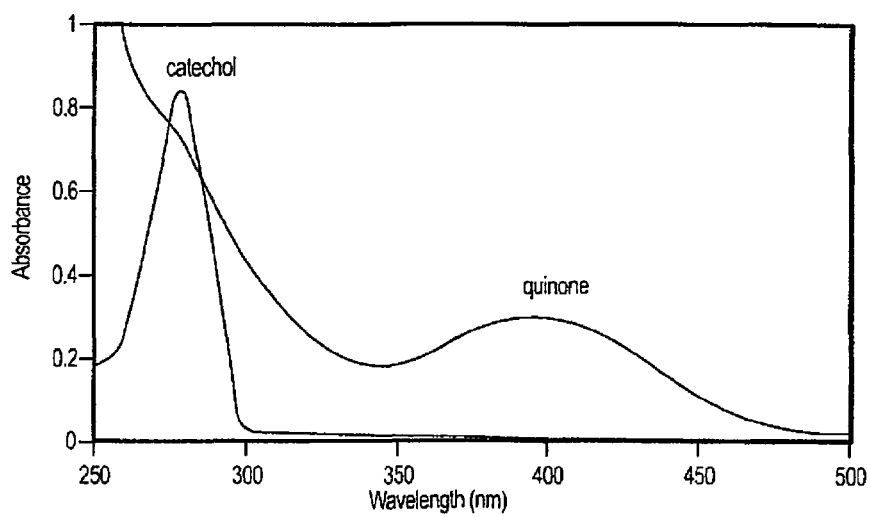

The MW and polydispersity index (PDI) of 1 were determined by SEC in DMF on a PLgel column (Polymer Labs) connected to a small angle light scattering detector (Brookhaven BI-MWA) and refractive index monitor (Brookhaven BI-DNDC). The column was calibrated with polystyrene standards. The MW of 1 was 245 kda with a PDI of 1.9. The dopamine sidechain concentration and reactivity was verified by UV/VIS spectroscopy ($e_{280}$=2600 M$^{-1}$ cm$^{-1}$). The phosphate sidechain concentration were determined by titration with 0.005 M NaOH using an automated titrator (Brinkmann Titrando 808). The UV/vis spectrum of 1 contained a single absorption peak at 280 nm characteristic of the catechol form of dopamine (FIG. 10B). Addition of a 1:1 molar ratio of NaIO$_4$ to 1 at pH 5.0 oxidized the dopa catechol to dopaquinone with an absorption peak near 395 nm as expected. The dopaquinone peak was stable for several hrs at pH<5.

Pc1 Analogs.

The lysine sidechains of Pc1 were mimicked with N-(3-aminopropyl)methacrylamide hydrochloride (APMA, Polysciences). Copolymer 2 (FIG. 10) was synthesized by dissolving 10 mol % APMA and 90 mol % Aam in DI water, degassing with N$_2$ and initiating polymerization with 2 mol % ammonium persulfate (Polysciences). Polymerization proceeded at 50° C. for 24 hrs in sealed ampules. Polymer was recovered by dialysis against water for 3 days, and then freeze dried. The primary amine sidechain mol % was determined by $^1$H NMR (400 MHz, DMSO-TMS) from the ratios of d 13.45 (3H, —CH3) and d 51.04 (1H, RC(=O)CHR2). The MW and PDI of 2 were determined by SEC in PBS (20 mM PO$_4$, 300 mM NaCl, pH 7.2) on a Superose 6 column (Pharmacia). The column was calibrated with poly-2-hydroxypropyl methacrylate standards. The MW of 2 was 165 kd and PDI was 2.4.

Coacervate Formation and Characterization.

A 5 wt % aqueous solution of 2 was added dropwise while stirring to a 5 wt % aqueous solution of 1 until reaching the target amine/phosphate ratio. Total copolymer concentration was 50 mg/ml. After mixing for 30 min the pH was adjusted with NaOH (6M). Compositions at pH (<4) conducive to polyelectrolyte complex (PEC) formation were diluted to 1 mg/ml in DI H$_2$O and the zeta potentials and size distribution of PECs were measured on a Zeta-Sizer 3000HS (Malvern Instruments). At higher pH, coacervated compositions were centrifuged at 2500 rpm in a microfuge (Eppendorf), at 25° C. for 2 min to collect the coacervate phase. The volume of both phases was measured. The coacervate phases were freeze dried and weighed to determine their mass and concentration.

Figure 11A:
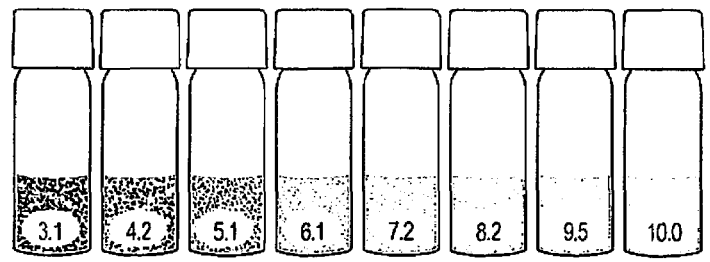
FIG. 11 shows the pH dependent complex coacervation of mixed polyelectrolytes. (A) At low pH, a 50 mg/ml mixture of 1 and 2 having equal quantities of amine and phosphate sidechains formed stable colloidal PECs. As the pH increased the polymers condensed into a dense liquid complex coacervate phase. At pH 10 the copolymers went into solution and oxidatively crosslinked into a clear hydrogel. (B) The net charge of the copolymer sidechains as a function of pH calculated from the copolymer sidechain densities. (C) The diameter of the PECs (circles) increased nearly three-fold over the pH range 2-4. Above pH 4 the complexes flocculate and their size could not be measured. The zeta potential (squares) was zero near pH 3.6 in agreement with the calculated net charge.
Figure 11B:
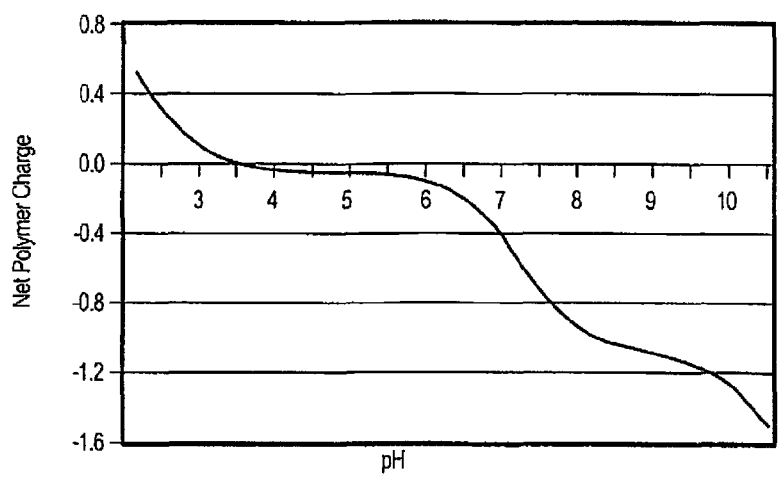
Figure 11C:
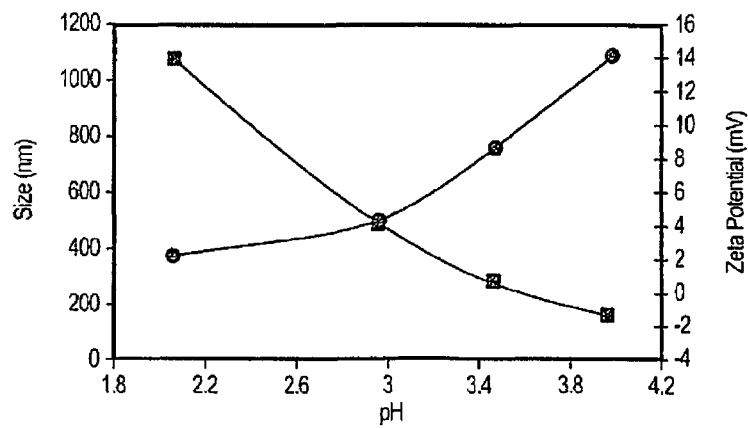

The phase behavior of 1 and 2 mixed at a 1:1 molar ratio of phosphate to amine sidechains (50 mg/ml combined concentration) over the pH range 3-10 is shown in FIG. 11A. The calculated net copolymer charge normalized to the total ionizable sidechain concentration is shown in FIG. 11B. Ascorbate, a reductant, was added at a 1:5 molar ratio to dopa to retard oxidation of dopa by O$_2$ and subsequent crosslinking at elevated pH. At low pH, the polyelectrolytes formed a stable milky solution of colloidal polyelectrolyte complexes (PECs). The mean diameter of the PECs at pH 2.1, determined by dynamic light scattering, was 360 nm with a narrow dispersity and increased to 1080 nm at pH 4.0 (FIG. 11C). The crossover of the zeta potential from positive to negative at pH 3.6 fit well with the calculated pH dependent net charge of the complexes (FIG. 11B). The particle size could not be measured accurately above pH 4 because the complexes flocculated. As the net charge increased due to the deprotonation of the phosphate sidechains, the copolymers condensed into a dense second phase. At pH 5.1 the separated phase had the character of a loose low density precipitate. At pH 7.2 and 8.3 the dense phase had the character of a cohesive liquid complex coacervate (FIG. 12). The copolymers were concentrated about three-fold to 148 and 153 mg/ml, respectively, in the coacervated phases. At pH 9.5 the polyelectrolyte mixture formed a dense non-liquid ionic gel. At pH 10 the copolymers went into solution and spontaneously crosslinked through the dopaquinone and amine sidechains into a clear hydrogel.

Figures 12A, 12B, 13:
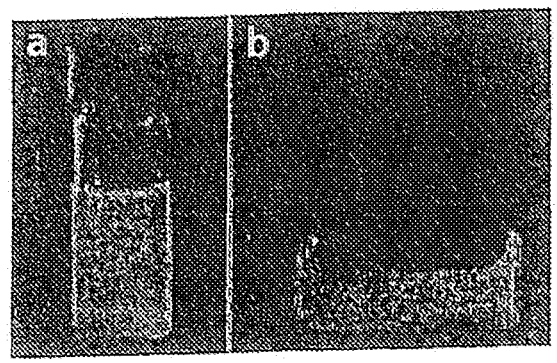
FIG. 13 shows the phase diagram of polyelectrolytes and divalent cations. The amine to phosphate sidechain and phosphate sidechain to divalent cation ratios were varied at a fixed pH 8.2. The state of the solutions represented in a gray scale. The mass (mg) of the coacervate phase is indicated in the dark grey squares. The compositions indicated with an asterisk were used to test bond strength.

Extraction of divalent cations with the chelator EDTA resulted in a 50% decrease in compressive strength of *P. californica* tubes, a ten-fold decrease in adhesiveness, and collapse of the glues porous structure. The effect of divalent cations on the phase behavior of the mimetic polyelectrolytes was investigated by mixing 1 and 2 at amine to phosphate sidechain ratios ranging from 1:1 to 0:1 with divalent cation to phosphate sidechain ratios ranging from 0:1 to 1:1 to create a coacervate phase diagram (FIG. 13). The pH was fixed at 8.2, the pH of seawater, and divalent cations were added as a 4:1 mixture of Mg$^{2+}$ and Ca$^{2+}$, the approximate Mg$^{2+}$/Ca$^{2+}$ ratio in the natural glue determined by elemental analysis. The highest mass of coacervate (dark gray squares) occurred in mixtures with higher amine to phosphate sidechain ratios and lower divalent cation to phosphate sidechain ratios. Mixtures with lower polyamine ratios were clear (clear squares) even at higher divalent cation/phosphate sidechain ratios. At higher amine/phosphate and divalent cation/phosphate ratios the solutions were turbid (light gray squares) with slight precipitates but much less turbid than solutions containing PECs (medium gray squares).

Mechanical Bond Testing.

Bone test specimens, ~1 cm$^3$, were cut with a band saw from bovine femur cortical bone, obtained from a local grocery store, sanded with 320 grit sandpaper, and stored at −20° C. NaIO$_4$ at a 1:2 molar ratio to dopa sidechains was evenly applied to one face each of two wet bone specimens. Forty ml, a volume sufficient to completely fill the space between 1 cm$^2$ bone interfaces, of the test coacervate solution was applied with a pipette, the bone specimens were pressed together squeezing out a small excess of adhesive, clamped, and immediately wrapped in PBS (20 mM PO$_4$, 150 mM NaCl, pH 7.4) soaked gauze. The applied coacervate contained ascorbate at a 1:5 molar ratio to dopa to prevent premature crosslinking. The bonded specimens were incubated at 37° C. for at least 24 hr in a sealed container containing soaked sponges to maintain 100% humidity. Reference specimens were bonded with 40 ml Loctite 401 superglue in exactly the same manner. A commercial non-medical grade cyanoacrylate was used because there are no hard tissue medical adhesives available for comparison. Mechanical tests were performed on a custom built material testing system using a 1 kg load cell. The instrument was controlled and data acquired using LabView (National Instruments). One bone of a bonded pair was clamped laterally 1 mm from the bond interface. The second bone was pressed with a cross-head speed of 0.02 mm/s against a dull blade positioned 1 mm lateral to the bond interface. Bond strength tests were performed at room temperature immediately after unwrapping the wet specimens to prevent drying. After testing, the bonds were examined for failure mode. The bonded area was measured by tracing an outline of the bone contact surface on paper, cutting out the trace, and determining its area from the weight of the paper cut-out. At least 6 specimens were tested for each condition.

Figure 14A:
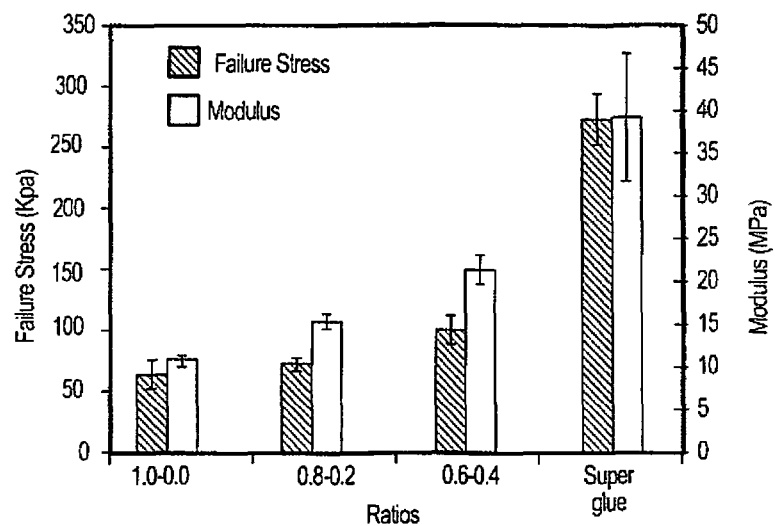
FIG. 14 shows the bond strength, shear modulus, and dimensional stability of coacervate bonded bones. (A) Bond strength at failure increased ~50% and the stiffness doubled as the divalent cation ratio went from 0 to 0.4 relative to phosphate sidechains. Specimens wet bonded with a commercial cyanoacrylate adhesive were used as a reference. (n=6 for all conditions) (B) Bonds of adhered bone specimens fully submerged in PBS for four months (pH 7.2) did not swell appreciably.
Figure 14B:
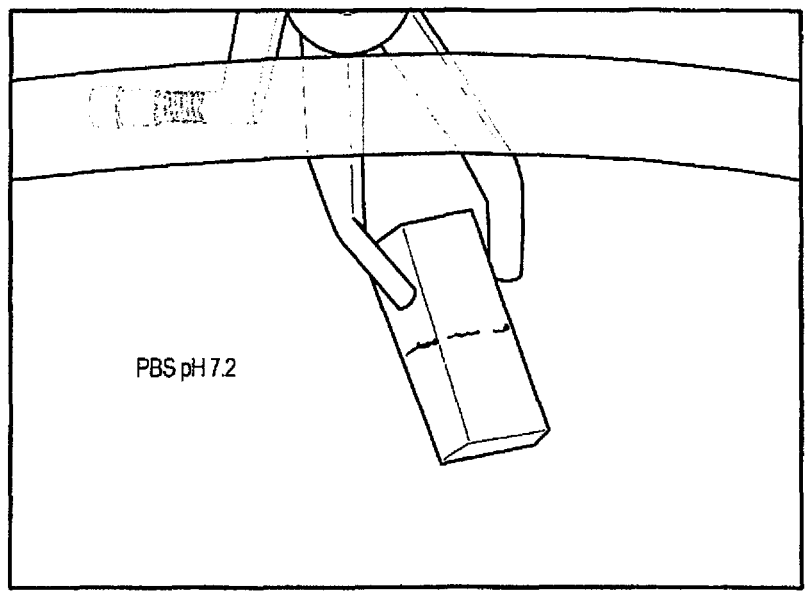

The shear modulus and strength at failure were measured with bovine cortical bone specimens bonded while wet with the three coacervating compositions marked with an asterisk in FIG. 13. The coacervate density in the three compositions increased with increasing divalent cation ratios (to 120, 125, and 130 mg/ml, respectively). Both the modulus and bond strength of the fully hydrated specimens increased with increasing divalent cation concentration, reaching 37% of the strength of wet bones bonded with a commercial cyanoacrylate adhesive (FIG. 14A). The cyanoacrylate adhesive was used as a reference point because there are no bone adhesives in clinical use for comparison. The strength of the mimetic adhesive is also about ⅓ the strength of natural *P. californica* glue estimated to be 350 kPa and mussel byssal glue estimated to range from 320 to 750 kPa dependent on the season. In almost all cases the bonds failed cohesively leaving adhesive on both bone interfaces, which suggested the compositions formed strong interfacial bonds with hydroxyapatite. The bonds were dimensionally stable, neither shrinking nor swelling appreciably after complete submersion in PBS pH 7.2 for several months (FIG. 14B). Dimensional stability during cure and long term exposure to water is an important requirement for a useful bone adhesive.

Dopamine-Mediated Copolymer Crosslinking.

Figure 15:
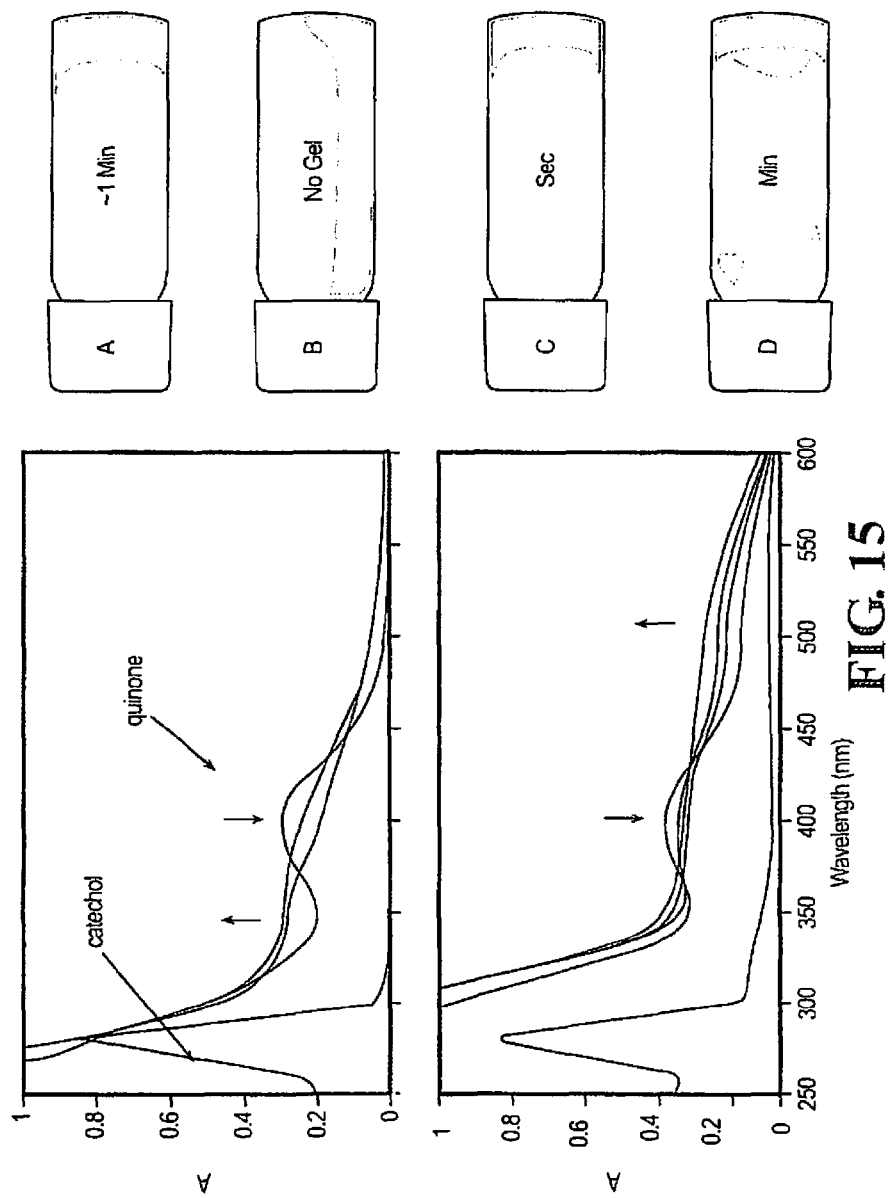
FIG. 15 shows UV-vis spectra of dopamine copolymers before and after oxidation (pH 7.2). A catechol peak present before oxidation was converted into the quinone form. Top left: p(DMA[8]-Aam[92]). Bottom left: p(AEMA[30]-DMA [8]). Right: Hydrogel formation by oxidative crosslinking of dopamine copolymers. (A) p(DMA[8]-Aam[92]). (B) p(EGMP[92]-DMA[8]). (C) p(DMA[8]-Aam[92]) mixed with p(AEMA[30]-Aam[70]). (D) p(EGMP[92]-DMA[8]) mixed with p(AEMA[30]-Aam[70]). Bracketed numbers indicate mol % of sidechains. Arrows indicate direction spectra are changing over time.

Addition of NaIO$_4$ to solutions of 3 at a 1:1 molar ratio immediately and quantitatively oxidized DOPA (280 nm) to dopaquinone (392 nm). Within a few minutes the quinine peak decayed into broad general absorption as the reactive quinones formed covalent diDOPA crosslinks (FIG. 15, top left). Crosslinking between the quinones and primary amines (FIG. 15, bottom left) led to a broader general absorption than diDOPA crosslinking Dopamine oxidation and crosslinking chemistry therefore behaved as expected in the dopamine copolymers. The dopamine copolymers rapidly formed hydrogels as a result of oxidative crosslinking (FIGS. 15, A&C). Oxidized phosphodopamine 3 did not gel by itself (FIG. 15B) but when mixed with 4 it gelled rapidly (FIG. 15D). Intermolecular diDOPA crosslinking between PO$_4$ copolymers was inhibited but not intermolecular DOPA-amine crosslinking. This provides a crosslinking control mechanism that may be useful for formulating and delivering a synthetic adhesive.

pH Triggered DOPA-Mediated Crosslinking.

Figure 16:
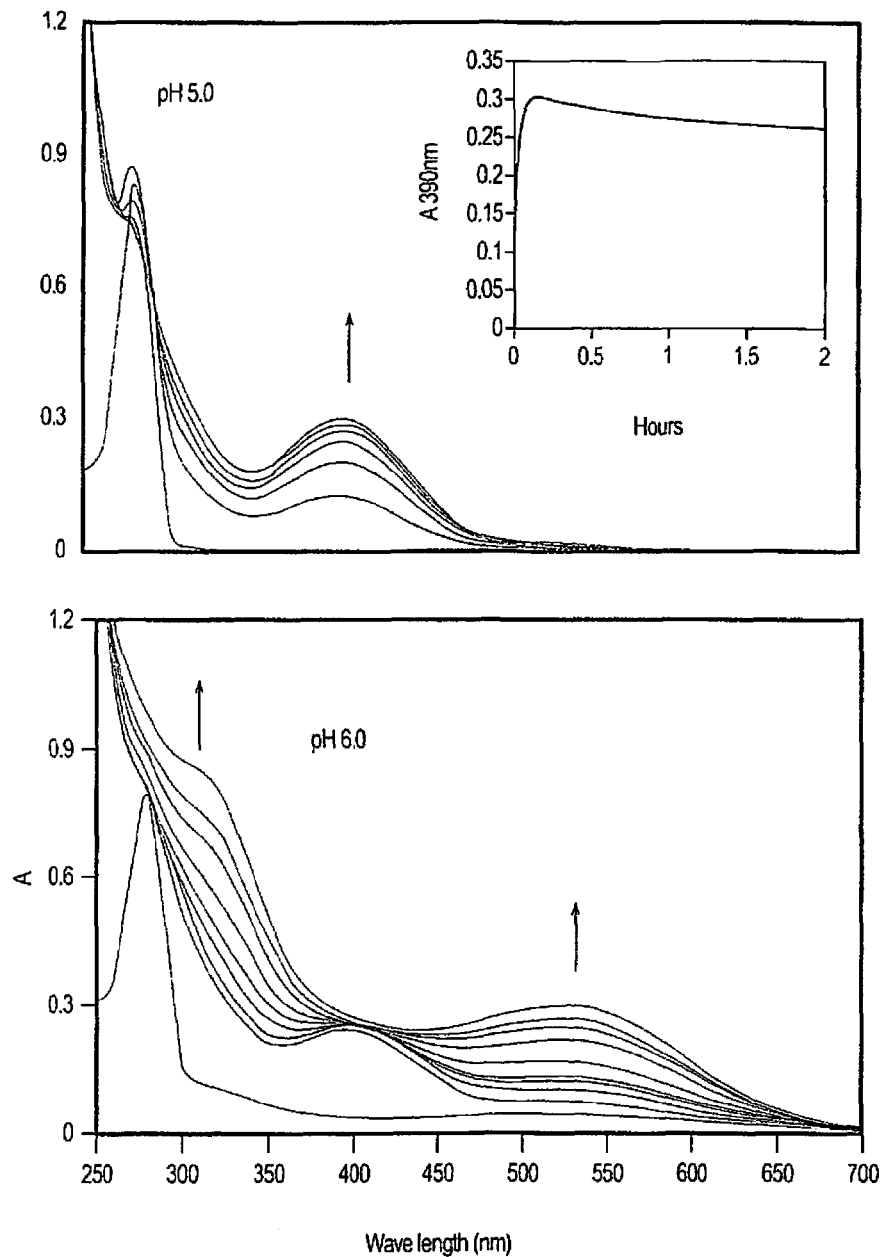
FIG. 16 shows pH dependence of dopamine oxidation in poly(EGMP[92]-DMA[8]). Arrows indicate direction spectra change with time. Top: pH 5.0, time course inset. Bottom: pH 6.0.

To explore, the pH dependence and kinetics of DOPA oxidation, crosslinking of the dopamine copolymers were evaluated by UV-Vis spectroscopy. Results with p(EGMP [92]-DMA[8]) (3) are shown in FIG. 16. UV-vis spectra were acquired at increasing time after addition of a stoichiometric amount of NaIO$_4$. At pH 5.0 (top), dopaquinone absorbance (398 nm) was maximal in ~15 min and remained stable for several hrs (inset). At pH 6.0, absorbance at 398 nm peaked in <1 min and evolved into broad absorbance with peaks at 310 and 525 nm. The broad absorbance is not due to dopaquinone crosslinking since gels do not form (FIG. 16). For comparison, 6 was oxidized at low pH crosslinked but at a significantly slower rate (not shown).

The results show that the dopaquinone is stable at low pH and diDOPA crosslinking was inhibited at higher pH in the phosphodopamine copolymers. In the presence of the polyamine, the covalent crosslinking was channeled toward intermolecular amine-DOPA bonds. This is an important observation because it lays out a path to controlled delivery and setting of the synthetic adhesive.

In Vitro Cytotoxicity.

Figures 17A, 17B, 17C:
FIG. 17 shows direct contact of (A) human foreskin fibroblasts, (B) human tracheal fibroblasts, and (C) rat primary astrocytes with adhesive (red auto-fluorescent chunks, white asterisks). Cell morphology, fibronectin secretion, and motility are indistinguishable from cells growing in the absence of glue. Green=intermediate filament proteins. Red=secreted fibronection. Blue=DAPI stained nuclei.

Solutions of 3 and 4, 40 wt % each, were mixed at low pH to form a polyelectrolyte complex. The solution was partially oxidized with NaIO$_4$ and basified with NaOH just before application to sterile glass coverslips. The adhesive-treated coverslips were placed in the bottom of culture plate wells and human foreskin fibroblasts, human tracheal fibroblasts, and rat primary astrocytes in serum containing media were added to separate wells at 30K cells/well (FIG. 17). After 24 hr, the cells were fixed with 4% para-formaldehdye, then immunostained for the intermediate filament protein, vimentin, to visualize cell morphology (green, A-B), pericellular fibronectin to assess ECM secretion (red, B), glial fibrillary protein to visual primary astrocyte morphology (green, C), and DAPI to visualize nuclei (blue, C). The granular globs of adhesive auto-fluoresced orangish-red (A-C).

In the representative images (FIG. 17), all cell types had morphologies indistinguishable from cells growing on glass without adhesive. The cells had normal motility and in several cases extended processes that directly contacted the adhesive. No toxicity was apparent.

Rat Calvarial Defect Model.

Figure 18A:
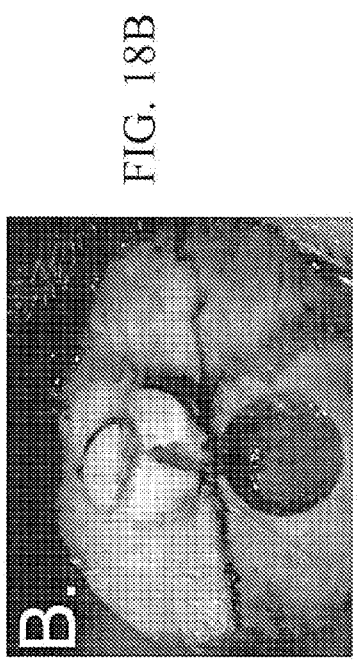
FIG. 18 shows a multi-fragment rat calvarial defect model. (A) Generation of defect. (B) Fragmentation of bone cap. (C) Replacement of fragments in defect. (D) Application of bone glue. (E-F) Curing (darkening) of glue. Fragments are firmly fixed in E and F.
Figure 18B:
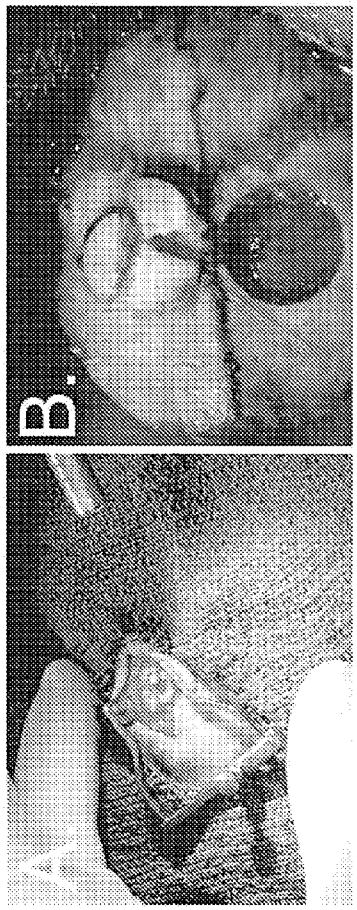
Figure 18C:
Figure 18D:
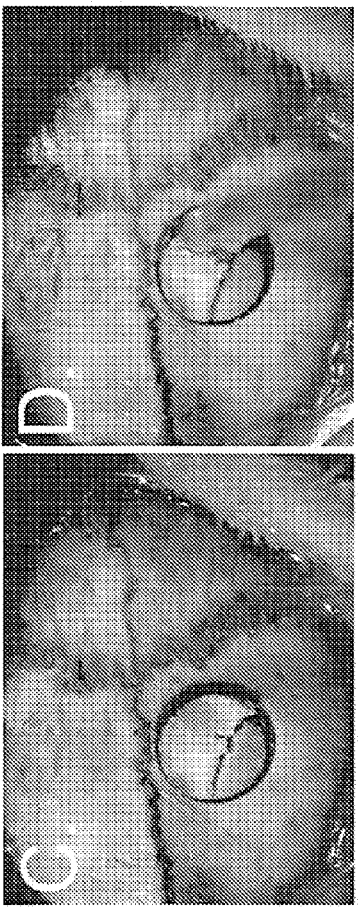
Figure 18E:
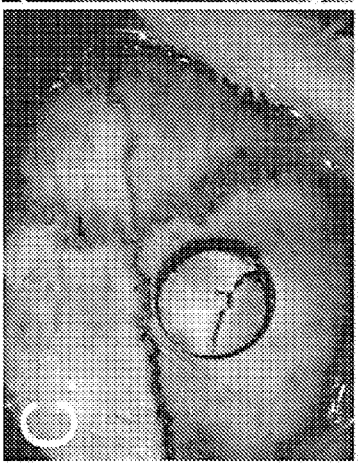
Figure 18F:
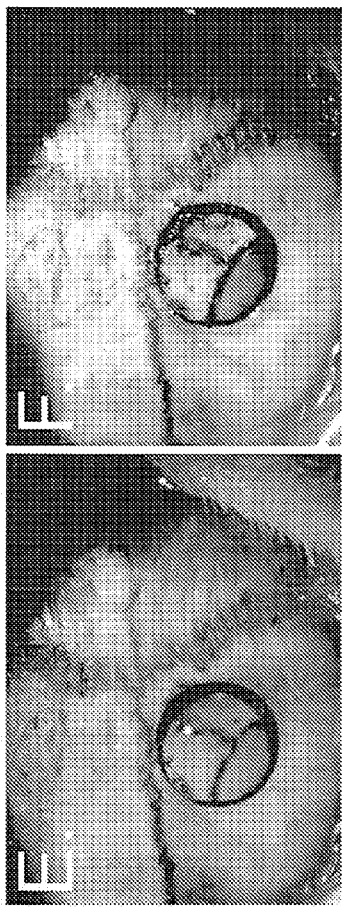
Figure 19:
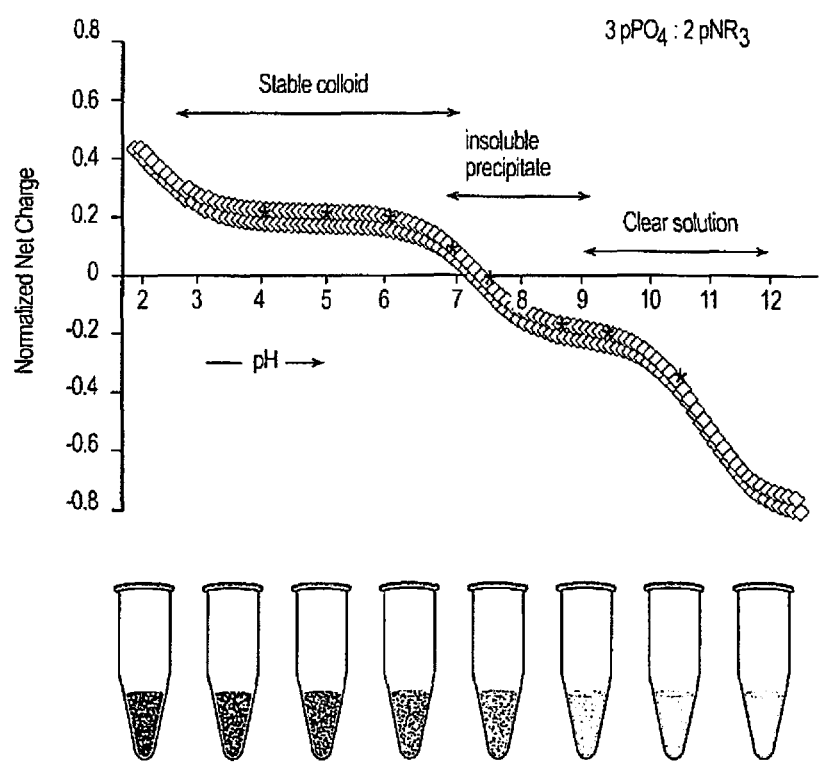
FIG. 19 shows the effect of pH and normalized net charge with respect to forming adhesive complex coacervates.

Production of the fragmented defect and repair with an adhesive complex coacervate is shown in FIGS. 18A-F. Male Sprague Dawley rats (256-290 g) (Harlan) were anesthetized with a mixture of ketamine (65 mg/kg), xylazine (7.5 mg/kg), and acepromazine (0.5 mg/kg). At full depth of anesthesia, the eyes were covered with ophthalmic ointment, the head shaved, and the scalp disinfected with isopropanol and butadiene. With the prepped rats in a stereotactic frame, a compressed air-driven drill operating at ~5000 RPM was lowered using a stereotactic fine toothed manipulator. Sterile saline or PBS was continuously applied at the craniotomy site while the custom made trephine tool was lowered 600 microns (previously determined as the skull thickness of rats the age of which were used in the experiment). The result is a round, accurate hole through the skull with little observable effect on the underlying dura or vasculature (FIG. 18A-B). The bone plug was recovered with fine curved forceps and broken into fragments using a hemostat and fine rongeur (FIG. 18B). The bone fragments were returned to the defect (FIG. 18C) and 5 μl of test adhesive (3 and 4 mixed immediately prior to the application of the fracture) was applied with a micropipettor (FIG. 18D). The low viscosity adhesive solution (pre-formed PECS mixed with curing solution just before delivery) readily and cleanly wicked into the fractures. Within 5 min the fragments were sufficiently fixed that they could be tapped sharply with the forceps without displacement. The adhesive continued to turn dark reddish brown as it cured (FIG. 18E-F).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. An adhesive comprising a complex coacervate, wherein the complex coacervate comprises at least one synthetic polycation, at least one synthetic polyanion, and at least one multivalent cation, wherein the synthetic polycation and the synthetic polyanion each comprise at least one crosslinkable group covalently bonded to the synthetic polycation and the synthetic polyanion capable of covalently crosslinking with one another.

2. The coacervate of claim 1, wherein the polycation comprises a polyamino compound.

3. The coacervate of claim 1, wherein the polycation comprises a polyacrylate comprising one or more pendant amino groups.

4. The coacervate of claim 1, wherein the polycation comprises a polyacrylate comprising one or more pendant imidazole groups.

5. The coacervate of claim 1, wherein the polycation comprises a polymer comprising at least one fragment comprising the formula I

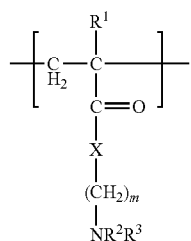

I wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof.

6. The coacervate of claim 5, wherein $R^1$, $R^2$, and $R^3$ are methyl, X is NH, and m is 2.

7. The coacervate of claim 2, wherein the polyamino compound comprises from 10 to 90 mole % primary, secondary, or tertiary amino groups.

8. The coacervate of claim 1, wherein the polyanion comprises one or more sulfate, sulfonate, carboxylate, borate, boronate, phosphonate, or phosphate groups.

9. The coacervate of claim 1, wherein the polyanion comprises a polyphosphate compound.

10. The coacervate of claim 1, wherein the polyanion comprises a polyacrylate comprising one or more pendant phosphate groups.

11. The coacervate of claim 1, wherein the polyanion comprises a polymer comprising at least one fragment comprising the formula II

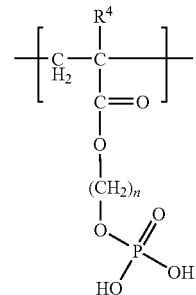

II wherein $R^4$ is hydrogen or an alkyl group, and n is from 1 to 10, or the pharmaceutically-acceptable salt thereof.

12. The coacervate of claim 11, wherein $R^4$ is methyl and n is 2.

13. The coacervate of claim 10, wherein the polyphosphate compound comprises from 10 to 90 mole % phosphate groups.

14. The coacervate of claim 1, wherein the polyanion comprises a polyphosphoserine.

15. The coacervate of claim 1, wherein the multivalent cation comprises one or more transition metal ions or rare earth metals.

16. The coacervate of claim 1, wherein the multivalent cation comprises one or more divalent cations.

17. The coacervate of claim 1, wherein the multivalent cation comprises $Ca^{+2}$ and $Mg^{+2}$.

18. The coacervate of claim 1, wherein the composition is biocompatible and biodegradable.

19. The coacervate of claim 1, wherein the composition further comprises one or more bioactive agents encapsulated in the complex.

20. The coacervate of claim 1, wherein the groups capable of crosslinking with one another are the same or different.

21. The coacervate of claim 1, wherein the crosslinking group on the polycation comprises a nucleophilic group and the crosslinking group on the polyanion comprises an electrophilic group.

22. The coacervate of claim 1, wherein the crosslinking group on the polycation and polyanion comprises a hydroxyl aromatic compound capable of undergoing oxidation.

23. The coacervate of claim 1, wherein the crosslinking group on the polyanion comprises a DOPA residue or a catechol residue and the polycation comprises a nucleophilic group capable of reacting with the crosslinking group to form a covalent bond.

24. An adhesive complex coacervate produced by the process comprising
  (a) preparing a polyelectrolyte complex comprising admixing at least one synthetic polycation, at least one synthetic polyanion, and at least one multivalent cation, and the synthetic polycation and synthetic polyanion each comprise at least one group capable of covalently crosslinking with each other; and
  (b) adjusting the pH of the polyelectrolyte complex, the concentration of the at least one divalent cation, or a combination thereof to produce the adhesive complex coacervate.

25. The coacervate of claim 24, wherein the coacervate is produced in situ.

26. The coacervate of claim 24, wherein step (a) is performed at a pH less than 4, and step (b) comprises raising the pH.

27. The coacervate of claim 24, wherein step (b) comprises raising the pH of the polyelectrolyte complex to a pH of greater than or equal to 7.0.

28. The coacervate of claim 24, wherein after step (b) further comprises contacting the complex coacervate with an oxidant in order to facilitate the crosslinking between the polycation and polyanion.

29. The coacervate of claim 28, wherein the oxidant comprises $O_2$, $NaIO_4$, a peroxide, or a transition metal oxidant.

30. A method for repairing a bone fracture in a subject, comprising contacting the fractured bone with the adhesive complex coacervate of claim 1 and covalently crosslinking the synthetic polycation and synthetic polyanion in the adhesive complex coacervate.

31. The method of claim 30, wherein the method is in vitro.

32. The method of claim 30, wherein the method is in vivo.

33. The method of claim 30, wherein the fracture comprises complete fracture, an incomplete fracture, a linear fracture, a transverse fracture, an oblique fracture, a compression fracture, a spiral fracture, a comminuted fracture, a compacted fracture, or an open fracture.

34. The method of claim 30, wherein the fracture comprises an intra-articular fracture.

35. The method of claim 30, wherein the fracture comprises a craniofacial bone fracture.

36. The method of claim 30, wherein the method comprises adhering a fractured piece of bone to an existing bone.

37. The method of claim 30, wherein the composition sets within 60 seconds.

38. A method for adhering a metal substrate to a bone of a subject comprising contacting the bone with the composition of claim 1, applying the metal substrate to the coated bone, and covalently crosslinking the synthetic polycation and synthetic polyanion in the adhesive complex coacervate.

39. A method for adhering a bone-tissue scaffold to a bone of a subject comprising contacting the bone and tissue with the composition of claim 1, applying the bone-tissue scaffold to the bone and tissue, and covalently crosslinking the synthetic polycation and synthetic polyanion in the adhesive complex coacervate.

40. The method of claim 39, wherein the tissue comprises cartilage, a ligament, a tendon, a soft tissue, an organ, or synthetic derivative thereof.

41. The method of claim 39, wherein the scaffold comprises one or more drugs that facilitate growth or repair of the bone and tissue.

42. A method for repairing a crack in a tooth, comprising applying the composition of claim 1 to the crack and covalently crosslinking the synthetic polycation and synthetic polyanion in the adhesive complex coacervate.

43. A method for securing a dental implant, comprising applying the composition of claim 1 to an oral substrate, attaching the dental implant to the substrate, and covalently crosslinking the synthetic polycation and synthetic polyanion in the adhesive complex coacervate.

44. The method of claim 43, wherein the dental implant comprises a crown or denture.

45. A method for delivering one or more bioactive agents comprising administering the coacervate of claim 1 to a subject.

46. The coacervate of claim 1, wherein the polycation comprises a polyamino compound and the polyanion comprises a polyphosphate compound.

* * * * *

SEQUENCE LISTING

```
<160> NUMBER OF SEQ ID NOS: 19

<210> SEQ ID NO 1
<211> LENGTH: 191
<212> TYPE: PRT
<213> ORGANISM: Phragmatopoma californica

<400> SEQUENCE: 1

Met Lys Val Phe Ile Val Leu Ala Leu Val Ser Ala Ala Tyr Gly Cys
1               5                   10                  15

Gly Val Gly Ile Gly Cys Ala Gly Gly Arg Cys Gly Gly Ala Cys Gly
            20                  25                  30

Gly Lys Gly Tyr Gly Tyr Gly Gly Lys Leu Gly Tyr Gly Ala Tyr Gly
        35                  40                  45

Lys Gly Gly Ile Gly Gly Tyr Gly Tyr Gly Lys Gly Cys Val Gly Gly
    50                  55                  60

Tyr Gly Tyr Gly Gly Leu Gly Ala Gly Lys Leu Gly Gly Tyr Gly Tyr
65                  70                  75                  80

Gly Gly Ser Lys Cys Gly Gly Tyr Gly Tyr Gly Gly Gln Lys Leu Gly
                85                  90                  95

Gly Tyr Gly Tyr Gly Gly Lys Lys Leu Gly Gly Tyr Gly Tyr Ala Ala
            100                 105                 110

Lys Lys Val Gly Gly Tyr Gly Tyr Gly Ala Lys Lys Val Gly Gly Tyr
        115                 120                 125

Gly Tyr Gly Ala Lys Lys Val Gly Gly Tyr Gly Tyr Gly Ala Lys Lys
    130                 135                 140

Val Gly Gly Tyr Gly Tyr Gly Ala Lys Lys Val Gly Gly Tyr Gly Tyr
145                 150                 155                 160

Gly Ala Lys Lys Val Gly Gly Tyr Gly Tyr Gly Ala Lys Lys Val Gly
                165                 170                 175

Gly Tyr Gly Tyr Gly Val Lys Lys Val Gly Gly Tyr Gly Tyr Gly
            180                 185                 190

<210> SEQ ID NO 2
<211> LENGTH: 210
<212> TYPE: PRT
<213> ORGANISM: Phragmatopoma californica

<400> SEQUENCE: 2

Met Lys Val Leu Ile Phe Leu Ala Thr Val Ala Ala Val Tyr Gly Cys
1               5                   10                  15

Gly Gly Ala Gly Gly Trp Arg Ser Gly Ser Cys Gly Gly Arg Trp Gly
            20                  25                  30

His Pro Ala Val His Lys Ala Leu Gly Gly Tyr Gly Gly Tyr Gly Ala
        35                  40                  45
```

```
His Pro Ala Val His Ala Ala Val His Lys Ala Leu Gly Gly Tyr Gly
    50                  55                  60

Ala Gly Ala Tyr Gly Ala Gly Ala Trp Gly His Pro Ala Val His Lys
 65                  70                  75                  80

Ala Leu Gly Gly Tyr Gly Ala Gly Ala Trp Gly His Pro Ala Val His
                 85                  90                  95

Lys Ala Leu Gly Gly Tyr Gly Gly Tyr Gly Ala His Pro Ala Val His
            100                 105                 110

Val Ala Val His Lys Ala Leu Gly Gly Tyr Gly Ala Gly Ala Cys Gly
                115                 120                 125

His Lys Thr Gly Gly Tyr Gly Gly Tyr Gly Ala His Pro Val Ala Val
            130                 135                 140

Lys Ala Ala Tyr Asn His Gly Phe Asn Tyr Gly Ala Asn Asn Ala Ile
145                 150                 155                 160

Lys Ser Thr Lys Arg Phe Gly Gly Tyr Gly Ala His Pro Val Val Lys
                165                 170                 175

Lys Ala Phe Ser Arg Gly Leu Ser His Gly Ala Tyr Ala Gly Ser Lys
                180                 185                 190

Ala Ala Thr Gly Tyr Gly Tyr Gly Ser Gly Lys Ala Ala Gly Gly Tyr
                195                 200                 205

Gly Tyr
    210

<210> SEQ ID NO 3
<211> LENGTH: 151
<212> TYPE: PRT
<213> ORGANISM: Phragmatopoma californica

<400> SEQUENCE: 3

Met Lys Leu Leu Ser Val Phe Ala Ile Val Val Leu Ala Val Tyr Ile
  1               5                  10                  15

Thr His Val Glu Ala Asp Ser Ser Ser Ser Tyr Ser Ser Ser Ser Ser
             20                  25                  30

Ser Tyr Ser Ser Ser Ser Ser Ser Ser Ser Ser Ser Ser Ser Ser Tyr
         35                  40                  45

Ser Ser Ser Ser Ser Tyr Ser Ser Ser Ser Ser Ser Ser Tyr Ser Ser
 50                  55                  60

Ser Ser Ser Tyr Ser Ser Ser Ser Ser Tyr Ser Ser Ser Ser Tyr Ser
 65                  70                  75                  80

Ser Ser Ser Tyr Ser Ser Ser Ser Tyr Ser Ser Ser Ser Ile Leu Thr
                 85                  90                  95

Ser Thr Ser Ser Ser Asp Trp Lys Arg Lys Val Pro Ala Arg Arg Val
            100                 105                 110

Leu Arg Thr Arg Arg Phe Leu Lys Cys Val Thr Arg Cys Thr Leu Arg
            115                 120                 125

Cys Ile Leu Phe Arg Ser Ala Lys Thr Cys Ala Arg Lys Cys Ser Arg
            130                 135                 140

Arg Cys Leu Lys Arg Val Phe
145                 150

<210> SEQ ID NO 4
<211> LENGTH: 342
<212> TYPE: PRT
<213> ORGANISM: Phragmatopoma californica

<400> SEQUENCE: 4
```

```
Met Lys Ser Phe Thr Ile Phe Ala Ala Ile Leu Val Ala Leu Cys Tyr
1               5                   10                  15

Ile Gln Ile Ser Glu Ala Gly Cys Cys Lys Arg Tyr Ser Ser Ser Ser
            20                  25                  30

Tyr Ser Ser Ser Ser Ser Ser Ser Ser Ser Tyr Ser Ser Ser Ser Ser
        35                  40                  45

Ser Ser Ser Ser Tyr Ser Ser Ser Ser Ser Ser Ser Tyr Ser Ser Ser
    50                  55                  60

Ser Ser Ser Ser Ser Ser Ser Tyr Ser Ser Ser Ser Ser Ser Ser Ser
65                  70                  75                  80

Tyr Ser Ser Ser Ser Ser Ser Tyr Ser Ser Ser Ser Ser Ser Ser Ser
                85                  90                  95

Ser Ser Ser Tyr Ser Ser Ser Ser Ser Tyr Ser Ser Ser Ser Ser Ser
            100                 105                 110

Ser Ser Ser Ser Tyr Ser Ser Ser Ser Ser Ser Ser Tyr Ser Ser Ser
                115                 120                 125

Ser Ser Ser Ser Ser Ser Ser Tyr Ser Ser Ser Ser Ser Ser Ser Ser
    130                 135                 140

Tyr Ser Ser Ser Ser Ser Ser Tyr Ser Ser Ser Ser Ser Ser Ser Ser
145                 150                 155                 160

Ser Ser Ser Tyr Ser Ser Ser Ser Ser Tyr Ser Ser Ser Ser Ser Ser
            165                 170                 175

Ser Ser Ser Tyr Ser Ser Ser Ser Ser Ser Ser Ser Tyr Ser Ser Ser
            180                 185                 190

Ser Ser Ser Ser Ser Tyr Ser Ser Ser Ser Ser Tyr Ser Ser Ser Ser
            195                 200                 205

Ser Ser Ser Ser Ser Ser Ser Tyr Ser Ser Ser Ser Ser Ser Ser Ser
    210                 215                 220

Ser Ser Ser Ser Tyr Ser Ser Ser Ser Ser Tyr Ser Ser Ser Ser Ser
225                 230                 235                 240

Ser Ser Ser Ser Ser Tyr Ser Ser Ser Ser Ser Ser Ser Ser Ser Tyr
                245                 250                 255

Ser Ser Ser Ser Ser Ser Ser Ser Tyr Ser Ser Ser Ser Ser Ser Ser
            260                 265                 270

Ser Ser Ser Ser Ser Tyr Ser Ser Ser Ser Ser Tyr Ser Ser Ser Ser
            275                 280                 285

Ser Ser Ser Ser Ser Tyr Ser Ser Ser Ser Ser Ser Ser Ser Ser Ser
        290                 295                 300

Tyr Ser Ser Ser Ser Ser Ser Tyr Ser Ser Ser Ser Ser Ser Ser Ser
305                 310                 315                 320

Ser Ser Ser Ser Tyr Ser Ser Ser Ser Ser Ser Ser Ser Ser Ser Ser
                325                 330                 335

Ser Ser Tyr Ser Ser Ser
            340

<210> SEQ ID NO 5
<211> LENGTH: 272
<212> TYPE: PRT
<213> ORGANISM: Phragmatopoma californica

<400> SEQUENCE: 5

Met Pro Thr Leu Tyr Lys Lys Val Gly Lys Leu Val Ile Leu Ala Ile
1               5                   10                  15

Ile Val Thr Val Ala Ser Val Ala Ser Ala Gly Tyr Pro Thr Tyr Ser
            20                  25                  30
```

Pro Ser Gly Gly Thr His Ser Gly Tyr Asn Gly Pro His Gly Asn Val
        35                  40                  45

Val Lys Lys Thr Tyr Arg Gly Pro Tyr Gly Ala Gly Ala Ala Lys Ala
 50                  55                  60

Trp Asn Gly Tyr His Gly Ala Gly Tyr Thr Ser Val His His Gly Pro
 65                  70                  75                  80

Ala Ser Thr Ser Trp His Thr Ser Trp Ser Asn Lys Lys Gly Gly Tyr
                85                  90                  95

Gly Tyr Gly Leu Lys Asn Lys Gly Tyr Gly Tyr Gly Leu Lys Lys Val
                100                 105                 110

Gly Tyr Gly Val Gly Leu His Ala Ala Gly Trp His Gly Val Gly Pro
                115                 120                 125

Tyr Gly Ala Gly Tyr His Gly Ala Gly Trp Asn Gly Leu Gly Tyr His
130                 135                 140

Gly Ala Gly Tyr Gly Val His Gly Val Gly Leu His Gly Ala Gly Tyr
145                 150                 155                 160

Gly Leu His Gly Val Gly Leu His Gly Val Gly Tyr Gly Leu His Gly
                165                 170                 175

Val Gly Leu His Gly Ala Gly Tyr Gly Leu His Gly Val Gly Leu His
                180                 185                 190

Gly Ala Gly Tyr Gly Ile His Gly Val Gly Leu His Gly Ala Gly Tyr
                195                 200                 205

Gly Ile His Gly Val Gly Leu His Gly Val Gly Tyr Gly Leu His Gly
            210                 215                 220

Val Gly Leu His Gly Ala Gly Tyr Gly Leu His Gly Val Gly Leu His
225                 230                 235                 240

Gly Ala Gly Tyr Gly Ile His Gly Val Gly Leu His Gly Ala Gly Cys
                245                 250                 255

Gly Ile His Lys Thr Ala Cys Tyr Gly Val Gly Leu His Gly His Tyr
                260                 265                 270

<210> SEQ ID NO 6
<211> LENGTH: 144
<212> TYPE: PRT
<213> ORGANISM: Phragmatopoma californica

<400> SEQUENCE: 6

Met Lys Phe Leu Val Leu Leu Ala Leu Val Ala Ser Ala Ser Ala Tyr
 1               5                  10                  15

Tyr Pro Leu Met Gly Gly Phe His Gly Gly Trp His Ala Pro Met Val
                20                  25                  30

His Gly Gly Leu Tyr His Gly Gly Trp His Ala Pro Met Val His Gly
                35                  40                  45

Gly Leu Tyr His Gly Gly Trp His Ala Pro Ile Val His Gly Gly Trp
 50                  55                  60

His Ala Pro Val Phe His Ala Pro Ala Pro Ile His Thr Val Ser His
 65                  70                  75                  80

Ser Val Val Asn His Val Pro Met Met Pro Met Trp His His Pro Ala
                85                  90                  95

Pro Ala Pro Ala Pro Ala Pro Arg Pro Gly Arg Thr Ile Ile Leu Gly
                100                 105                 110

Gly Gly Lys Tyr Gly Pro Phe Gly Lys Tyr Gly Gly Ala Gly Leu
                115                 120                 125

Leu Ala Leu Gly Ala Leu Gly Gly Asn Gly Gly Phe Trp Lys Arg Arg

-continued

<210> SEQ ID NO 7
<211> LENGTH: 328
<212> TYPE: PRT
<213> ORGANISM: Phragmatopoma californica

<400> SEQUENCE: 7

Met Leu Phe Tyr Asn Ala Asn Phe Val Gln Lys Ser Trp Val Leu Ile
1               5                   10                  15

Leu Leu Gly Leu Ala Ala Val Val Ala Cys Ser Glu Tyr Asp Lys Gly
            20                  25                  30

Leu Gly Gly Tyr Gly Arg Pro Ser Tyr Gly Gly Arg Arg Gly Tyr Gly
        35                  40                  45

Gly Arg Arg Gly Leu Gln Tyr His Gly Lys Tyr Gln Gly Arg Cys Glu
    50                  55                  60

Tyr Asp Gly Leu Tyr Phe Arg Asp Glu Lys Ser Phe Val Tyr Cys Ser
65                  70                  75                  80

Asn Arg Asn Ser Tyr Ile Gln Pro Cys Ala Pro Gly Thr Arg Asn Ser
                85                  90                  95

Pro Tyr Thr Lys Tyr Asn Arg Gly Ser Lys Tyr Asn Tyr Arg Asp Phe
            100                 105                 110

Cys Glu Val Asn Leu Val Asp Ser Gly Tyr Val Pro Lys Pro Gly Tyr
        115                 120                 125

Leu Pro Ala Pro Lys Lys Ala Tyr Pro Thr Lys Val Tyr Asp Leu Lys
    130                 135                 140

Val Asp Tyr Ala Pro Lys Val Asp Tyr Ala Pro Lys Val Asp Tyr Ala
145                 150                 155                 160

Pro Lys Val Asp Tyr Ala Pro Lys Val Asp Tyr Val Ala Pro Lys Ala
                165                 170                 175

Ser Tyr Val Pro Pro Lys Ala Ser Tyr Val Asp Pro Thr Pro Thr Tyr
            180                 185                 190

Gly Tyr Glu Ala Pro Phe Lys Gly Gly Tyr Asp Lys Pro Ser Tyr Gly
        195                 200                 205

Lys Asp Val Asp Thr Ser Tyr Glu Ser Lys Thr Thr Tyr Thr Val Glu
210                 215                 220

Lys Thr Ala Asp Lys Gly Tyr Gly Lys Gly Tyr Gly Asp Lys Glu Ile
225                 230                 235                 240

Ser Ala Lys Lys Ser Tyr Thr Leu Thr Glu Lys Arg Asp Tyr Asp Thr
                245                 250                 255

Gly Tyr Asp Asn Ser Arg Ser Asp Glu Asp Ser Lys Glu Tyr Gly Tyr
            260                 265                 270

Asp Asn Asp Arg Ser Glu Ser Tyr Glu Arg Thr Glu Ser Tyr Thr Asp
        275                 280                 285

Glu Arg Thr Asp Gly Tyr Gly Thr Gln Lys Val Glu Tyr Thr Gln Gln
    290                 295                 300

Ser Glu Tyr Asp Arg Val Thr Arg Arg Gly Ile Trp Leu His Lys Gly
305                 310                 315                 320

Thr Glu Val Glu His Val Leu Tyr
                325

<210> SEQ ID NO 8
<211> LENGTH: 136
<212> TYPE: PRT
<213> ORGANISM: Phragmatopoma californica
<220> FEATURE:

<221> NAME/KEY: misc_feature
<222> LOCATION: (49)..(49)
<223> OTHER INFORMATION: Xaa can be any naturally occurring amino acid

<400> SEQUENCE: 8

```
Met Asn Thr Phe Val Val Leu Ala Ala Ile Val Ala Val Ala Ala Cys
1               5                   10                  15

Ser Gly Gly Tyr Asp Gly Arg Gln Tyr Thr Tyr Arg Gly Arg Tyr Asn
            20                  25                  30

Asn Lys Cys Gly Asn Asp Gly Leu Tyr Phe Lys Asp Lys Asn Phe
        35                  40                  45

Xaa Phe Cys Ser Asn Gly Asn Ser Tyr Val Gln Pro Cys Ala Pro Gly
    50                  55                  60

Thr Arg Asn Ser Gly Tyr Asn Asn Tyr Lys Gln Gly Ser Ile Tyr Asn
65                  70                  75                  80

Tyr Arg Asp Phe Cys Asp Val Asn Leu Val Asp Glu Gly Tyr Gly Val
                85                  90                  95

Gly Ala Lys Pro Gly Tyr Asn Lys Gly Tyr Asn Pro Gly Tyr Asn Pro
            100                 105                 110

Gly Tyr Gly Gly Tyr Asn Pro Gly Tyr Ser Thr Gly Tyr Gly Gly Tyr
        115                 120                 125

Lys Ala Gly Pro Gly Pro Tyr Trp
    130                 135
```

<210> SEQ ID NO 9
<211> LENGTH: 158
<212> TYPE: PRT
<213> ORGANISM: Phragmatopoma californica

<400> SEQUENCE: 9

```
Met Lys Leu Ala Leu Leu Leu Val Ala Val Cys Ala Ala Val Ala
1               5                   10                  15

Val Asn Ala Cys Gly Pro Leu Gly Cys Ser Gly Gly Tyr Gly Gly Val
            20                  25                  30

Leu Lys Cys Gly Val Gly Gly Cys Ala Leu Gly Gly Tyr Gly Gly Gly
        35                  40                  45

Tyr Ser Ala Gly Ile Gly Gly Tyr Gly Ile Lys Arg Leu Gly Cys Arg
    50                  55                  60

Gly Gly Arg Cys Gly Leu Arg Arg Val Gly Cys Arg Gly Arg
65                  70                  75                  80

Cys Gly Leu Arg Gly Arg Leu Gly Cys Arg Gly Gly Arg Cys Gly Leu
                85                  90                  95

Arg Lys Leu Gly Cys Arg Gly Gly Arg Cys Gly Leu Arg Gly Arg Leu
            100                 105                 110

Gly Cys Arg Gly Gly Arg Cys Gly Leu Arg Lys Arg Leu Gly Cys Arg
        115                 120                 125

Gly Gly Arg Cys Gly Arg Gly Gly Tyr Gly Gly Tyr Gly Gly Val
    130                 135                 140

Cys Ser Lys Gly Val Cys Gly Gly Tyr Pro Ala Tyr Gly Lys
145                 150                 155
```

<210> SEQ ID NO 10
<211> LENGTH: 236
<212> TYPE: PRT
<213> ORGANISM: Phragmatopoma californica

<400> SEQUENCE: 10

```
Met Lys Val Ser Ile Ala Val Leu Ile Met Cys Cys Ile Ala Ala Val
1               5                   10                  15

Leu Ala Asp Gly Tyr Lys Ser Lys Asn Gly Gly Gln Ala Gly Gly Tyr
                20                  25                  30

Gly Gly Tyr Gly Ser Gly Tyr Gly Gly Tyr Gly Gly Gly Tyr Asp
        35                  40                  45

Gly Gly Tyr Gly Gly Glu Lys Gly Lys Ser Gly Lys Gly Tyr Gly Asp
50                  55                  60

Arg Lys Gly Lys Ser Glu Lys Gly Tyr Gly Asn Gly Lys Gly Lys Gly
65                  70                  75                  80

Gly Ser Gly Tyr Gly Gly Tyr Asp Gly Tyr Gly Gly Lys
                85                  90                  95

Gly Lys Ser Gly Ser Gly Tyr Gly Gly Gly Tyr Asp Gly Gly Tyr Gly
                100                 105                 110

Gly Gly Lys Gly Lys Ser Gly Ser Gly Tyr Gly Gly Tyr Asp Gly
            115                 120                 125

Gly Tyr Asp Gly Gly Tyr Gly Gly Lys Gly Lys Ser Gly Ser Gly
        130                 135                 140

Phe Gly Gly Tyr Asp Gly Gly Tyr Asp Gly Gly Tyr Gly Gly Gly
145                 150                 155                 160

Lys Gly Lys Ser Gly Ser Gly Tyr Gly Gly Tyr Asp Gly Tyr
                165                 170                 175

Asp Gly Gly Tyr Gly Gly Lys Gly Lys Ser Gly Ser Gly Tyr Gly
            180                 185                 190

Gly Gly Tyr Asp Gly Gly Tyr Asp Gly Gly Tyr Gly Gly Lys Gly
        195                 200                 205

Lys Ser Gly Ser Gly Tyr Gly Gly Tyr Asp Gly Gly Tyr Asp Gly
210                 215                 220

Arg Tyr Gly Gly Gly Lys Gly Lys Ser Gly Ser Gly
225                 230                 235

<210> SEQ ID NO 11
<211> LENGTH: 191
<212> TYPE: PRT
<213> ORGANISM: Phragmatopoma californica

<400> SEQUENCE: 11

Met Lys Leu Ile Cys Leu Val Leu Leu Ala Val Cys Ile Val Ala Val
1               5                   10                  15

Ser Ala Ser Ser Ser Gly Gly Arg Arg Arg Arg Val Ile Val Ile
                20                  25                  30

Gly Asn Arg Gly Arg Ala Pro Ala Arg Pro Arg Ser Asn Ile His Tyr
        35                  40                  45

His Met His Ala Pro Gln Pro Arg Met Met Met Ala Pro Arg Met Met
        50                  55                  60

Met Ala Pro Met Met Met Ala Pro Met Ala Met Pro Ala Thr Ser His
65                  70                  75                  80

Val Tyr Gln Ser Val Ser Tyr Pro Gly Ala Met Tyr Arg Tyr Gly Leu
                85                  90                  95

Gly Ser Leu Gly Gly Gly Phe Ile Ser Gly Gly Leu Gly Gly Ile Val
                100                 105                 110

Gly Gly Gly Leu His Gly Gly Val Val Thr Ser Gly Leu His Gly Gly
            115                 120                 125
```

```
Val Val Thr Ser Gly Leu His Gly Gly Val Val Thr Ser Gly Leu His
        130                 135                 140

Gly Gly Leu Val Ser Gly Gly Trp His Ser Gly Val Val Ser His Gly
145                 150                 155                 160

Gly Leu Ile Gly Gly Ile His Thr Thr Tyr Gly Gly Phe His Lys
            165                 170                 175

Gly Val Val His Gly Gly Tyr Thr Gly His Tyr Gly Lys Arg Arg
            180                 185                 190

<210> SEQ ID NO 12
<211> LENGTH: 102
<212> TYPE: PRT
<213> ORGANISM: Phragmatopoma californica

<400> SEQUENCE: 12

Met Lys Leu Ala Val Phe Ala Leu Leu Val Ala Phe Ala Ile Val Tyr
1               5                   10                  15

Thr Ala Glu Gly Leu Val Tyr Gly Gly Gln Lys Gly Tyr Gly Tyr Gly
            20                  25                  30

Gly Lys Gly Tyr Gly Tyr Gly Cys Thr Gly Gly Tyr Gly Leu Tyr Gly
        35                  40                  45

Gly Lys Gly Tyr Gly Tyr Gly Lys Gly Tyr Tyr Gly Cys Arg Gly
    50                  55                  60

Gly Tyr Gly Tyr Gly Lys Gly Tyr Tyr Gly Gly Lys Tyr Arg Gly
65                  70                  75                  80

Tyr Gly Tyr Gly Asn Lys Val Gly Tyr Gly Tyr Gly Gln Gln Leu Gly
                85                  90                  95

Tyr Lys Asn Gly Arg Lys
            100

<210> SEQ ID NO 13
<211> LENGTH: 91
<212> TYPE: PRT
<213> ORGANISM: Phragmatopoma californica

<400> SEQUENCE: 13

Leu Asp Gly Gly Cys Lys Pro Thr Gly Gly Phe Ile Lys Gly Ser Val
1               5                   10                  15

Gly Pro Cys Gly Gly Tyr Asn His Gln His Val Gly Pro Asn Gly
            20                  25                  30

Ala His Gly Arg Arg Val Gly Tyr Gly Pro Asn Gly Lys Tyr Ser Gln
        35                  40                  45

Ile Tyr Gly Asn Gly Pro Gly Gly Arg Tyr Ser His Thr Val Val Tyr
    50                  55                  60

Pro Arg Val Arg Pro Tyr Gly Tyr Gly Phe Lys Gly Gly Tyr Gly
65                  70                  75                  80

Gly Tyr His Gly Val Gly Tyr Lys Gly Gly Tyr
                85                  90

<210> SEQ ID NO 14
<211> LENGTH: 145
<212> TYPE: PRT
<213> ORGANISM: Phragmatopoma californica

<400> SEQUENCE: 14

Met Lys Val Phe Val Ala Ala Leu Leu Leu Cys Cys Ile Ala Ala Ala
1               5                   10                  15
```

```
Ala Ala Glu Asp Gly Tyr Gly Phe Gly Tyr Asp Gly Tyr Gly Ser Gly
            20                  25                  30

Tyr Gly Tyr Asp Gly Tyr Ser Tyr Gly Gly Asp Lys Gly Tyr Gly Tyr
        35                  40                  45

Gly Lys Gly Lys Gly Tyr Gly Tyr Glu Gly Gly Lys Gly Tyr Gly Tyr
    50                  55                  60

Glu Gly Gly Lys Gly Tyr Gly His Glu Glu Gly Lys Gly Tyr Gly His
65                  70                  75                  80

Glu Gly Gly Lys Gly Tyr Gly Tyr Glu Gly Gly Lys Gly Tyr Gly Tyr
                85                  90                  95

Gly Gly Gly Lys Gly Tyr Gly His Asp Gly Gly Lys Gly Tyr Gly His
            100                 105                 110

Asp Gly Gly Lys Gly Tyr Gly Tyr Gly Gly Gly Lys Gly Tyr Gly His
        115                 120                 125

Glu Gly Gly Lys Gly Tyr Gly Tyr Glu Gly Gly Lys Gly Tyr Gly Lys
    130                 135                 140

Tyr
145

<210> SEQ ID NO 15
<211> LENGTH: 134
<212> TYPE: PRT
<213> ORGANISM: Phragmatopoma californica

<400> SEQUENCE: 15

Met Arg Ile Val Ile Cys Leu Leu Val Leu Val Ala Gly Ala Tyr Gly
1               5                   10                  15

Ile Gly Cys Gly Tyr Gly Gly Tyr Gly Gly Tyr Gly Gly Gly Phe His
            20                  25                  30

Gly Gly Tyr Ile Gly Tyr His Gly Gly Tyr Pro Gly Tyr Ser Gly Gly
        35                  40                  45

Phe Arg Gly Tyr Gly Tyr Pro Gly Arg Val His Thr Asn Val Val His
    50                  55                  60

His Asn Ile Pro Val Phe Met Pro Pro Met Pro Arg Arg Ala Pro
65                  70                  75                  80

Ala Pro Ala Pro Arg Gly Arg Thr Ile Ile Leu Gly Gly Lys Tyr
                85                  90                  95

Gly Leu Phe Gly Lys Lys Ser Lys Asn Lys Gly Phe Gly Gly Leu Gly
            100                 105                 110

Val Leu Ser Leu Leu Gly Leu Gly Gly Lys Gly Gly Gly Ile
        115                 120                 125

Arg Phe Leu Gly Arg Lys
    130

<210> SEQ ID NO 16
<211> LENGTH: 226
<212> TYPE: PRT
<213> ORGANISM: Phragmatopoma californica

<400> SEQUENCE: 16

Met Lys Val Ile Ile Leu Leu Ala Thr Val Ala Ala Val Tyr Gly Cys
1               5                   10                  15

Gly Gly Trp Asn Gly Gly Phe Gly Gly Gly Lys Ala Cys Gly Gly Gly
            20                  25                  30
```

Trp Gly Ala Lys Ala Leu Gly Gly Tyr Gly Ser Tyr Asn Gly Asn Gly
            35                  40                  45

Tyr Gly Ala His Pro Val Ala Val Lys Ser Ala Phe Asn Lys Gly Val
    50                  55                  60

Ser Tyr Gly Ala Arg Ser Ala Val Lys Ala Thr Arg Gly Phe Ala Tyr
65                  70                  75                  80

Gly Lys Gly Ser Ser Tyr Gly Tyr Gly Ala His Pro Ala Val Lys Ser
                85                  90                  95

Ala Phe Gly Asn Gly Phe Lys Thr Gly Ala His Ala Ala Val Asn Gly
            100                 105                 110

Tyr Gly Tyr Gly Ala Val Lys Ser Ala Leu Ser Gly Tyr Gly Tyr
            115                 120                 125

Gly Ser Tyr Gly Ala His Pro Ala Val Lys Ser Ala Tyr Arg Lys Gly
    130                 135                 140

Leu Ser Tyr Gly Ala Lys Ser Ala Val Lys Ala Thr Arg Gly Phe Ala
145                 150                 155                 160

Tyr Gly Arg Ser Gly Tyr Gly Ala His Pro Val Val Lys Ser Ala Phe
                165                 170                 175

Ser Asn Gly Phe Lys Tyr Gly Ala His Ala Ala Val Lys Ala Thr Asn
            180                 185                 190

Gly Tyr Gly Tyr Gly Ala Val His Pro Ala Val Lys Ala Ala Val Lys
        195                 200                 205

Gly Gly Tyr Gly Tyr Gly Asn Lys Gly Gly Tyr Gly Ala Gly Tyr Ala
    210                 215                 220

Ala Tyr
225

<210> SEQ ID NO 17
<211> LENGTH: 89
<212> TYPE: PRT
<213> ORGANISM: Phragmatopoma californica

<400> SEQUENCE: 17

Met Lys Val Phe Val Ala Thr Leu Leu Leu Cys Cys Ile Ala Ala Ala
1               5                   10                  15

Ala Ala Ala Gly Tyr Gly Asn Gly Tyr Ala Gly Tyr Gly Ser Gly Tyr
            20                  25                  30

Ala Gly Tyr Gly Thr Gly Tyr Ala Gly Tyr Gly Ser Gly Tyr Gly Tyr
        35                  40                  45

Asp Gly Tyr Gly Tyr Gly Gly Lys Gly Tyr Gly Tyr Gly Gly Asp
    50                  55                  60

Lys Gly Tyr Gly Tyr Gly Gly Lys Gly Tyr Gly Tyr Gly Gly Gln Lys
65                  70                  75                  80

Gly Tyr Gly Tyr Gly Tyr Gly Lys Tyr
                85

<210> SEQ ID NO 18
<211> LENGTH: 105
<212> TYPE: PRT
<213> ORGANISM: Phragmatopoma californica

<400> SEQUENCE: 18

Met Lys Leu Leu Leu Leu Phe Ala Leu Ala Ala Val Ala Val Ala Leu
1               5                   10                  15

Pro Tyr Gly Tyr Ser Gly Lys Pro Gly Tyr Gly Tyr Asp Ala Val Asp
            20                  25                  30

```
Ala Val Tyr Asn Arg Leu Ala Asp Lys Gln Gln Ala Val Asn Arg Lys
            35                  40                  45

Ala Glu Tyr Val Gly Ala Gly Thr Gly Thr Ala Lys Tyr Asn Gly Val
    50                  55                  60

Pro Gly Ala Asn Tyr Gly Tyr Glu Asn Asp Arg Lys Tyr Gly Tyr Asp
65                  70                  75                  80

Asn Lys Gly Tyr Gly Tyr Gly Asp Lys Gly Tyr Gly Gly Tyr Gly
                85                  90                  95

Asp Lys Gly Leu Tyr Asp Gly Tyr Tyr
            100                 105

<210> SEQ ID NO 19
<211> LENGTH: 275
<212> TYPE: PRT
<213> ORGANISM: Phragmatopoma californica

<400> SEQUENCE: 19

Lys Tyr Tyr Asp Asp Glu Lys Arg Asp Ala Asp Lys Tyr Arg Lys Pro
1               5                   10                  15

Ser Tyr Asn Pro Tyr Asn Thr Tyr Lys Asp Tyr Pro Pro Lys Lys Ile
            20                  25                  30

Tyr Asn Asp Asp Glu Lys Arg Asp Ala Asp Gln Tyr Arg Ile Ser Tyr
            35                  40                  45

Asn Pro Tyr Asn Thr Tyr Lys Asp Tyr Pro Pro Lys Lys Tyr Tyr
    50                  55                  60

Asp Asp Glu Lys Arg Asp Ala Tyr Lys Tyr Arg Asn Pro Ser Tyr Asn
65                  70                  75                  80

Pro Tyr Asn Thr Tyr Lys Asp Tyr Pro Pro Lys Lys Ile Tyr Tyr Asp
                85                  90                  95

Asp Glu Lys Arg Asp Ala Asp Gln Tyr Arg Asn Pro Ser Tyr Asn Pro
                100                 105                 110

Tyr Asn Thr Tyr Lys Asp Tyr Pro Pro Lys Lys Lys Tyr Tyr Asp Asp
            115                 120                 125

Glu Lys Arg Asp Ala Asp Gln Tyr Arg Asn Pro Ser Tyr Asn Pro Tyr
130                 135                 140

Asn Thr Tyr Lys Asp Tyr Leu Pro Lys Lys Lys Tyr Tyr Asp Asp Glu
145                 150                 155                 160

Lys Arg Asp Ala Asp Gln Tyr Arg Lys Pro Ser Tyr Asn Pro Tyr Asn
            165                 170                 175

Ser Tyr Lys Asp Tyr Pro Pro Lys Lys Tyr Tyr Asp Asp Glu Lys
            180                 185                 190

Arg Asp Ala Asp Gln Tyr Arg Asn Pro Ser Tyr Asn Pro Tyr Asn Thr
            195                 200                 205

Tyr Lys Asp Tyr Leu Pro Lys Lys Tyr Tyr Asp Asp Glu Lys Arg
    210                 215                 220

Asp Ala Asp Gln Tyr Arg Asn Pro Ser Tyr Asn Pro Tyr Asn Thr Tyr
225                 230                 235                 240

Lys Asp Tyr Pro Pro Lys Lys Lys Tyr Tyr Asp Asp Glu Lys Arg Asp
                245                 250                 255

Ala Asp Gln Tyr Arg Asn Pro Ser Tyr Asn Pro Tyr Asn Thr Tyr Lys
            260                 265                 270

Asp Tyr Pro
    275
```